(12) United States Patent
Kasagi et al.

(10) Patent No.: US 11,446,247 B2
(45) Date of Patent: *Sep. 20, 2022

(54) LIPOSOME COMPOSITION AND PHARMACEUTICAL COMPOSITION

(71) Applicant: FUJIFILM Corporation, Tokyo (JP)

(72) Inventors: Noriyuki Kasagi, Ashigarakami-gun (JP); Naoki Yamada, Ashigarakami-gun (JP); Mikinaga Mori, Ashigarakami-gun (JP); Takayuki Kato, Ashigarakami-gun (JP); Takayuki Kobayashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/079,759

(22) Filed: Oct. 26, 2020

(65) Prior Publication Data

US 2021/0038518 A1 Feb. 11, 2021

Related U.S. Application Data

(63) Continuation of application No. 16/583,518, filed on Sep. 26, 2019, which is a continuation of application No. PCT/JP2018/013783, filed on Mar. 30, 2018.

(30) Foreign Application Priority Data

Mar. 31, 2017 (JP) .............................. JP2017-069836

(51) Int. Cl.
*A61K 9/127* (2006.01)
*A61K 33/02* (2006.01)
(Continued)

(52) U.S. Cl.
CPC ............ *A61K 9/1272* (2013.01); *A61K 33/02* (2013.01); *A61K 47/28* (2013.01); *A61K 31/4745* (2013.01)

(58) Field of Classification Search
CPC ...... A61K 9/1272; A61K 33/02; A61K 47/28; A61K 31/4745; A61K 47/02;
(Continued)

(56) References Cited

U.S. PATENT DOCUMENTS 5,192,549 A 3/1993 Barenolz et al.
5,543,152 A 8/1996 Webb et al.
(Continued)

FOREIGN PATENT DOCUMENTS

CN 102764234 A 11/2012
CN 104771361 A 7/2015
(Continued)

OTHER PUBLICATIONS

Zeghari-Squalli, N., et al in Clinical Cancer Research, vol. 5, pp. 1189-1196, 1999.*
(Continued)

*Primary Examiner* — Gollamudi S Kishore
(74) *Attorney, Agent, or Firm* — Sughrue Mion, PLLC

(57) ABSTRACT

An object of the present invention is to provide a liposome composition and a pharmaceutical composition, which exhibit a high AUC. Provided are a liposome composition including a hydrophilic polymer-modified diacylphosphatidylethanolamine, a dihydrosphingomyelin, and cholesterols as components of a liposome membrane, in which the liposome composition encapsulates a drug, an inner water phase thereof contains ammonium sulfate, and a molar ratio of sulfate ions in the inner water phase to the drug in an entire water phase is 0.36 or more; and a pharmaceutical composition including the liposome composition.

15 Claims, 4 Drawing Sheets

(51) Int. Cl.
*A61K 47/28* (2006.01)
*A61K 31/4745* (2006.01)

(58) Field of Classification Search
CPC .. A61K 9/1271; A61K 31/404; A61K 31/704; A61K 9/127; A61K 47/24; A61P 35/00
See application file for complete search history.

(56) References Cited

U.S. PATENT DOCUMENTS

| | | | |
|---|---|---|---|
| 6,355,268 | B1 | 3/2002 | Slater et al. |
| 7,060,828 | B2 | 6/2006 | Madden et al. |
| 7,811,602 | B2 | 10/2010 | Cullis et al. |
| 2006/0008909 | A1* | 1/2006 | Cullis ............... A61K 9/1272 435/458 |
| 2007/0231379 | A1* | 10/2007 | Slater ............... A61K 9/0019 514/253.02 |
| 2008/0075762 | A1 | 3/2008 | Tardi et al. |
| 2008/0206139 | A1 | 8/2008 | Connor et al. |
| 2009/0217401 | A1 | 8/2009 | Korman et al. |
| 2009/0285878 | A1 | 11/2009 | Hope et al. |
| 2011/0064794 | A1 | 3/2011 | Deng et al. |
| 2011/0159080 | A1 | 6/2011 | Lowery |
| 2011/0274625 | A1 | 11/2011 | Redelmeier et al. |
| 2013/0052259 | A1* | 2/2013 | Barenholz ............ A61K 31/4745 264/4.1 |
| 2013/0202686 | A1 | 8/2013 | Yamashita et al. |
| 2015/0030672 | A1 | 1/2015 | Li et al. |
| 2015/0258085 | A1* | 9/2015 | Bankiewicz ......... A61P 43/00 514/283 |
| 2016/0194625 | A1 | 7/2016 | Hoge et al. |
| 2017/0020816 | A1 | 1/2017 | Nagy et al. |
| 2017/0282144 | A1 | 10/2017 | Sugiyama et al. |
| 2018/0243214 | A1 | 8/2018 | Kitahashi et al. |
| 2020/0016079 | A1 | 1/2020 | Kasagi et al. |
| 2021/0100791 | A1 | 4/2021 | Shimoyama et al. |
| 2021/0213051 | A1 | 7/2021 | Okada et al. |

FOREIGN PATENT DOCUMENTS

| | | |
|---|---|---|
| EP | 0 361 894 A2 | 4/1990 |
| EP | 1 750 673 B1 | 12/2009 |
| JP | H 02-196713 A | 8/1990 |
| JP | 2659136 B2 | 9/1997 |
| JP | 2006-340714 A | 12/2006 |
| JP | 2008-519045 A | 6/2008 |
| JP | 2016-117005 A | 6/2016 |
| JP | 2017-512840 A | 5/2017 |
| WO | 2006/121168 A1 | 11/2006 |
| WO | 2012/091054 A1 | 7/2012 |
| WO | 2013/059922 A1 | 5/2013 |
| WO | 2017/078008 A1 | 5/2017 |
| WO | 2017/079303 A1 | 5/2017 |
| WO | 2018/083470 A1 | 5/2018 |
| WO | 2018/106729 A1 | 6/2018 |
| WO | 2018/181963 A1 | 10/2018 |

OTHER PUBLICATIONS

U.S. Appl. No. 17/125,336, filed Dec. 17, 2020 (Shimoyama).
U.S. Appl. No. 16/583,518, filed Sep. 26, 2019 (Kasagi).
International Preliminary Report on Patentability with translation of Written Opinion for PCT/JP2019/038708 dated Mar. 23, 2021, corresponding to U.S. Appl. No. 17/219,064.
International Search Report for PCT/JP2019/038708 dated Dec. 10, 2019 [PCT/ISA/210], corresponding to U.S. Appl. No. 17/219,064.
Office Action dated May 11, 2021 in U.S. Appl. No. 16/583,518.
Written Opinion of the International Searching Authority for PCT/JP2019/038708 dated Dec. 10, 2019 [PCT/ISA/237], corresponding to U.S. Appl. No. 17/219,064.
Zeghari-Squalli et al., "Cellular Pharmacology of the Combination of the DNA Topoisomerase I Inhibitor SN-38 and the Diaminocyclohexane Platinum Derivative Oxaliplatin", Clinical Cancer Research, May 1999, vol. 5, pp. 1189-1196 (9 pages total).
U.S. Appl. No. 17/219,064, filed Mar. 31, 2021 (Okada et al.).
Abraham et al., "An evaluation of transmembrane ion gradient-mediated encapsulation of topotecan within liposomes", Journal of Controlled Release, vol. 96, Issue 3, May 18, 2004, pp. 449-461, Abstract Only (3 pages total).
Xu Lili, "Preparation and in vitro and in vivo evaluation of topotecan hydrochloride liposomes", Wanfang, Sep. 17, 2014 (88 pages total).
Office Action dated Feb. 26, 2021, from the Intellectual Property of India in Indian application No. 202048031732, a divisional corresponding to U.S. Appl. No. 16/583,518 & 17/079,759 (the present application).
Office Action dated Feb. 22, 2021, from the Korean Intellectual Property Office in Korean application No. 10-2019-7028183, corresponding to U.S. Appl. No. 16/583,518.
Office Action dated Mar. 3, 2021, from the China National Intellectual Property Administration in Chinese application No. 201880023073.9, corresponding to U.S. Appl. No. 16/583,518.
Office Action dated Apr. 21, 2020, from the Russian Intellectual Property Office in Russian Application No. 2019130500/04.
Office Action dated Apr. 28, 2020, from the Australian Patent Office in Australian application No. 2018246024.
Extended European Search Report dated Feb. 24, 2020 from the European Patent Office in European application No. 18776957.5.
Office Action dated Mar. 19, 2020, from the Intellectual Property of India in Indian application No. 201947039515.
Fritze, A. et al., "Remote loading of doxorubicin into liposomes driven by a transmembrane phosphate gradient", Biochimica et Biophysica Acta, vol. 1758, No. 10, 2006, pp. 1633-1640.
Haran, G., et al., "Transmembrane ammonium sulfate gradients in liposomes produce efficient and stable entrapment of amphipathic weak bases", Biochimica et Biophysica Acta, vol. 1151, No. 2, XP023352276, 1993, pp. 201-215.
M. L. Immordino et al., "Stealth liposomes: review of the basic science, rationale, and clinical applications, existing and potential", International Journal of Nanomedicine, vol. 1. No. 3, pp. 297-315, 2006 (19 pages total).
International Preliminary Report on Patentability with English Translation of Written Opinion of the International Searching Authority for PCT/JP2018/013783 dated Oct. 1, 2019.
International Search Report for PCT/JP2018/013783 dated May 1, 2018 [PCT/ISA/210].
Michael Johnson et al., "Characterization of the drug retention and pharmacokinetic properties of liposomal nanoparticles containing dihydrosphingomyelin", Biochimica et Biophysica Acta, 2007, 1768, pp. 1121-1127 (total 7 pages).
Noble, C., et al., "Characterization of highly stable lipsomal and immunolipsomal formulations of vincristine and vinblastine", Cancer Chemotherapy and Pharmacology, 2009, vol. 64, No. 4, pp. 741-751.
Written Opinion for PCT/JP2018/013783 dated May 1, 2018 [PCT/ISA/237].
William C. Zamboni et al., "A Pharmacokinetic Study of a Novel Sphingomyelin/Cholesterol Liposomal Topotecan and Non-Liposomal Topotecan in Rats", AACR-NCI-EORTC International Conference, San Francisco, California, Oct. 22-26-2007, #C113, total 1 page.
Zasadzinski, J., et al., "Novel methods of enhanced retention in and rapid, targeted release from liposomes", Current Opinion in Colloid & Interface Science, vol. 16, No. 3, 2011, pp. 203-214.
Extended European Search Report dated Aug. 17, 2021 in European Application No. 19869479.6, corresponding to U.S. Appl. No. 17/219,064.
Yasuyuki Sadzuka et al., "Effect of Polyethyleneglycol (PEG) Chain on Cell Uptake of PEG-Modified Liposomes", Journal of Liposome Research, 2003, vol. 13, No. 2, pp. 157-172 (16 pages total).
U.S. Appl. No. 17/079,759 (the present application), Pending.
Bowen, P., "Particle Size Distribution Measurement from Millimeters to Nanometers and from Rods to Platelets", Journal of Dispersion Science and Technology, 2002, vol. 23, No. 5, pp. 631-662 (33 pages).

(56) References Cited

OTHER PUBLICATIONS

Extended European Search Report dated Jul. 1, 2021 in European Application No. 19823228.2, corresponds to U.S. Appl. No. 17/125,336.
Office Action dated Jun. 23, 2021 from the Brazilian Patent Office in Application No. BR112019020406-7, corresponding to U.S. Appl. No. 16/583,518.
Silverman et al., "In vitro experiments showing enhanced release of doxorubicin from Doxil® in the presence of ammonia may explain drug release at tumor site", Nanomedicine: Nanotechnology, Biology, and Medicine, vol. 11, 2015, pp. 1841-1850 (14 pages total).
Fugit et al., "Ion-Pairing Contribution to the Liposomal Transport of Topotecan as Revealed by Mechanistic Modeling", Journal of Pharmaceutical Sciences, vol. 106, 2017, pp. 1149-1161.
International Search Report for PCT/JP2019/024500 dated Aug. 27, 2019 PCT/ISA/210, corresponding to U.S. Appl. No. 17/125,336.
Written Opinion for PCT/JP2019/024500 dated Aug. 27, 2019 PCT/ISA/210, corresponding to U.S. Appl. No. 17/125,336.
International Preliminary Report on Patentability with English Translation of Written Opinion of the International Searching Authority for PCT/JP2019/024500 dated Dec. 22, 2020, corresponding to U.S. Appl. No. 17/125,336.
Office Action dated Jan. 10, 2020 in U.S. Appl. No. 16/583,518.
Office Action dated Jul. 24, 2020 in U.S. Appl. No. 16/583,518.
Office Action dated Sep. 24, 2021 in U.S. Appl. No. 16/583,518.
Communication dated Sep. 10, 2021 from the China National Intellectual Property Administration in Chinese Application No. 201880023073.9, corresponds to U.S. Appl. No. 16/583,518.
Notice of Reasons for Refusal dated Nov. 9, 2021 from the Japanese Patent Office in Japanese Application No. 2020-525795, corresponds to U.S. Appl. No. 16/583,518.
Office Action dated Mar. 1, 2022 from the Japanese Patent Office in Japanese Application No. 2020-550444, corresponding to U.S. Appl. No. 17/219,064.
U.S. Appl. No. 16/583,518, Pending.
U.S. Appl. No. 17/079,759, Pending.
U.S. Appl. No. 17/125,336, Pending.
U.S. Appl. No. 17/219,064, Pending.
Office Action dated Apr. 26, 2022 in Chinese Application No. 201980040973.9; corresponds to U.S. Appl. No. 17/125,336.
Notice of Allowance dated Mar. 16, 2022 in U.S. Appl. No. 16/583,518.
Office Action dated Jun. 22, 2022 in Chinese Application No. 201980064960.5, corresponds to U.S. Appl. No. 17/219,064.
Xu Leilei, Preparation and Pharmacokinetics in Rats of Topotecan Hydrochloride Liposomes by Ammonium Sulfate Gradient Method, Chinese Journal of Pharmaceuticals, 2014, vol. 45, No. 12, pp. 1139-1142 (4 pages total).

* cited by examiner

LIPOSOME COMPOSITION AND PHARMACEUTICAL COMPOSITION

CROSS-REFERENCE TO RELATED APPLICATIONS

This application is a Continuation of application Ser. No. 16/583,518 filed Sep. 26, 2019, which is continuation of PCT International Application No. PCT/JP2018/013783 filed on Mar. 30, 2018, which claims priority under 35 U.S.C § 119(a) to Japanese Patent Application No. 2017-069836 filed on Mar. 31, 2017. Each of the above application(s) is hereby expressly incorporated by reference, in its entirety, into the present application.

BACKGROUND OF THE INVENTION

1. Field of the Invention

The present invention relates to a liposome composition and a pharmaceutical composition, which exhibit high retention in blood.

2. Description of the Related Art

It is often studied that a drug is accumulated at a disease site such as cancer and exposed thereto over a long period of time by means of a liposome composition. In a liposome composition as a pharmaceutical composition, a drug is encapsulated in a liposome constituted of a lipid membrane.

Patent Document 1 and Non-Patent Document 1 disclose a liposome in which topotecan is encapsulated in a liposome containing sphingomyelin and cholesterol.

Patent Document 2 discloses a liposome in which topotecan is encapsulated in a liposome containing dihydrosphingomyelin and cholesterol.

Patent Document 3 discloses a liposomal camptothecin formulation adapted to enhance the stability of camptothecin, including (a) camptothecin encapsulated in a liposome, (b) first solution which is external to the liposome and has a pH of 4.5 or less than 4.5, and (c) second solution which is internal to the liposome. It is also disclosed that the liposome contains dihydrosphingomyelin and cholesterol.

Patent Document 4 discloses a system for effectively loading an amphiphilic drug into a liposome, including adjusting a liposome suspension in the presence of an ammonium compound or ammonium salt, diluting the suspension with a buffer or salt, and providing an ammonium gradient from the inside to the outside between an inner aqueous phase and an outer aqueous phase and a pH gradient such that the pH of the inside of the liposome is more acidic than the pH of the outside of the liposome.

Patent Document 5 discloses a liposome in which topotecan is encapsulated in the presence of ammonium sulfate in a liposome containing purified hydrogenated soybean phospholipid or sphingomyelin, cholesterol, and a hydrophilic polymer derivative lipid.

PATENT DOCUMENTS

Patent Document 1: U.S. Pat. No. 7,060,828B2
Patent Document 2: U.S. Pat. No. 7,811,602B2
Patent Document 3: JP2008-519045A
Patent Document 4: JP1990-196713A (JP-H02-196713A)
Patent Document 5: U.S. Pat. No. 6,355,268B2
Non-Patent Document 1: AACR-EORTC International Conference, San Francisco, Calif., Oct. 22-26, 2007, #C113 A Pharmacokinetics Study of a Novel Sphingomyelin/Cholesterol Liposomal Topotecan and Non-Liposomal Topotecan in Rats, William C. Zamboni et al.

SUMMARY OF THE INVENTION

The above-mentioned Patent Documents 1, 2 and 3 and Non-Patent Document 1 disclose that the drug efficacy is improved by encapsulating topotecan in a liposome containing sphingomyelin or dihydrosphingomyelin to suppress the leakage of topotecan in blood and improve the area under the blood concentration-time curve (AUC). However, since the composition of lipids that constitute the liposome and the composition of salts that precipitate topotecan have not been optimized, the improvement in AUC is not sufficient and therefore further improvement is required for AUC.

In addition, in a case where topotecan leaks out from the inner water phase of the liposome to the outer water phase and is then exposed to neutral conditions, the topotecan turns into analogs thereof. Specifically, an N—N bis adduct with extremely low solubility (topotecan amine dimer) or the like may be precipitated as crystals. Ultimately, many insoluble particulates that deviate from the safety and quality standards defined by the US Food and Drug Administration (FDA), Japan's Pharmaceutical and Medical Device Agency (PMDA), and the European Medicines Agency (EMEA) are formed, which is therefore not desirable. In order to suppress the formation of such insoluble particulates, the pH of the outer water phase is set to an acidic condition in Patent Document 3. However, in a case where the outer water phase is in the acidic condition, the decomposition of the lipids constituting the liposome is promoted, which is disadvantageous for the stabilization of the liposome. In the liposome of Patent Document, since it is necessary to acidify the outer water phase, it is difficult to add acid hydrolyzable methoxypolyethylene glycol-modified diacylphosphatidylethanolamine to improve retention in blood.

An object of the present invention is to provide a liposome composition and a pharmaceutical composition, which exhibit a high AUC.

As a result of extensive studies to achieve the foregoing object, the present inventors have found that it is possible to provide a liposome composition that achieves the foregoing object by a configuration that a hydrophilic polymer-modified diacylphosphatidylethanolamine, a dihydrosphingomyelin, and cholesterols are used as components of a liposome membrane, an inner water phase thereof contains ammonium sulfate, and a molar ratio of sulfate ions in the inner water phase to the drug in an entire water phase is set to be 0.36 or more. The present invention has been completed based on these findings.

That is, the present invention provides the following.

[1] A liposome composition comprising: a hydrophilic polymer-modified diacylphosphatidylethanolamine; a dihydrosphingomyelin; and cholesterols as components of a liposome membrane, in which the liposome composition encapsulates a drug, an inner water phase thereof contains ammonium sulfate, and a molar ratio of sulfate ions in the inner water phase to the drug in an entire water phase is 0.36 or more.

[2] The liposome composition according to [1], in which the drug is topotecan or a salt thereof, doxorubicin or a salt thereof, irinotecan or a salt thereof, or sunitinib or a salt thereof.

[3] The liposome composition according to [1] or [2], in which the molar ratio of sulfate ions in the inner water phase to the drug in the entire water phase is 0.6 or more and 1.8 or less.

[4] The liposome composition according to any one of [1] to [3], in which the hydrophilic polymer-modified diacylphosphatidylethanolamine is a polyethylene glycol- or methoxy polyethylene glycol-modified diacylphosphatidylethanolamine.

[5] The liposome composition according to any one of [1] to [4], in which the percentage of the hydrophilic polymer-modified diacylphosphatidylethanolamine in the components of the liposome membrane is 2 to 10 mol %.

[6] The liposome composition according to any one of [1] to [5], in which the percentage of cholesterols in the components of the liposome membrane is 35 to 43 mol %.

[7] The liposome composition according to any one of [1] to [6] which has a particle size of 150 nm or less.

[8] The liposome composition according to any one of [1] to [7], in which the outer water phase has a pH of 5.5 to 8.5.

[9] The liposome composition according to any one of [1] to [8], in which the dihydrosphingomyelin is a dihydrosphingomyelin containing a long-chain alkyl group having 16 carbon atoms and a long-chain alkyl group having 18 carbon atoms, and the encapsulated medicine is topotecan or a salt thereof.

[10] The liposome composition according to any one of [1] to [9], in which the percentage of the sulfate ions contained in the inner water phase of the liposome to the sulfate ions in the entire liposome composition is at least 80%, and the percentage of the drug contained in the inner water phase of the liposome to the drug in the entire liposome composition is at least 80%.

[11] The liposome composition according to [9], in which a drug release rate from the liposome in plasma having an ammonium concentration of 1 mmoL/L or less is 20%/24 hours or less at 37° C., and the drug release rate from the liposome in plasma having an ammonium concentration of 4 to 6 mmoL/L is 60%/24 hours or more at 37° C.

[12] The liposome composition according to any one of [1] to [11], in which the number of particles of more than 10 µm contained in 1 µmol of lipid of the liposome composition after storage for 1 month at 5° C. is 150 or less, and the number of particles of more than 25 µm contained in 1 µmol of lipid of the liposome composition is 15 or less.

[13] A pharmaceutical composition comprising:
the liposome composition according to any one of [1] to [12].

[14] The pharmaceutical composition according to [13], which is an anticancer agent.

[15] A liposome composition comprising: a hydrophilic polymer-modified diacylphosphatidylethanolamine; a dihydrosphingomyelin; and cholesterols as components of a liposome membrane, in which the liposome composition encapsulates a drug, an inner water phase thereof contains ammonium sulfate, and the dihydrosphingomyelin is a dihydrosphingomyelin containing a long-chain alkyl group having 16 carbon atoms and a long-chain alkyl group having 18 carbon atoms.

[A] A method for treating a disease, comprising administering to a subject, a liposome composition comprising a hydrophilic polymer-modified diacylphosphatidylethanolamine, a dihydrosphingomyelin, and cholesterols as components of a liposome membrane, in which the liposome composition encapsulates a drug, an inner water phase thereof contains ammonium sulfate, and a molar ratio of sulfate ions in the inner water phase to the drug in an entire water phase is 0.36 or more.

[B] A liposome composition for use in the treatment of a disease (preferably, cancer), comprising a hydrophilic polymer-modified diacylphosphatidylethanolamine, a dihydrosphingomyelin, and cholesterols as components of a liposome membrane, in which the liposome composition encapsulates a drug, an inner water phase thereof contains ammonium sulfate, and a molar ratio of sulfate ions in the inner water phase to the drug in an entire water phase is 0.36 or more.

[C] Use of a liposome composition for producing a pharmaceutical composition, comprising a hydrophilic polymer-modified diacylphosphatidylethanolamine, a dihydrosphingomyelin, and cholesterols, in which the liposome composition encapsulates a drug, an inner water phase thereof contains ammonium sulfate, and a molar ratio of sulfate ions in the inner water phase to the drug in an entire water phase is 0.36 or more.

The liposome composition and the pharmaceutical composition of the present invention can exhibit a high AUC.

DESCRIPTION OF THE PREFERRED EMBODIMENTS

Figure 1:
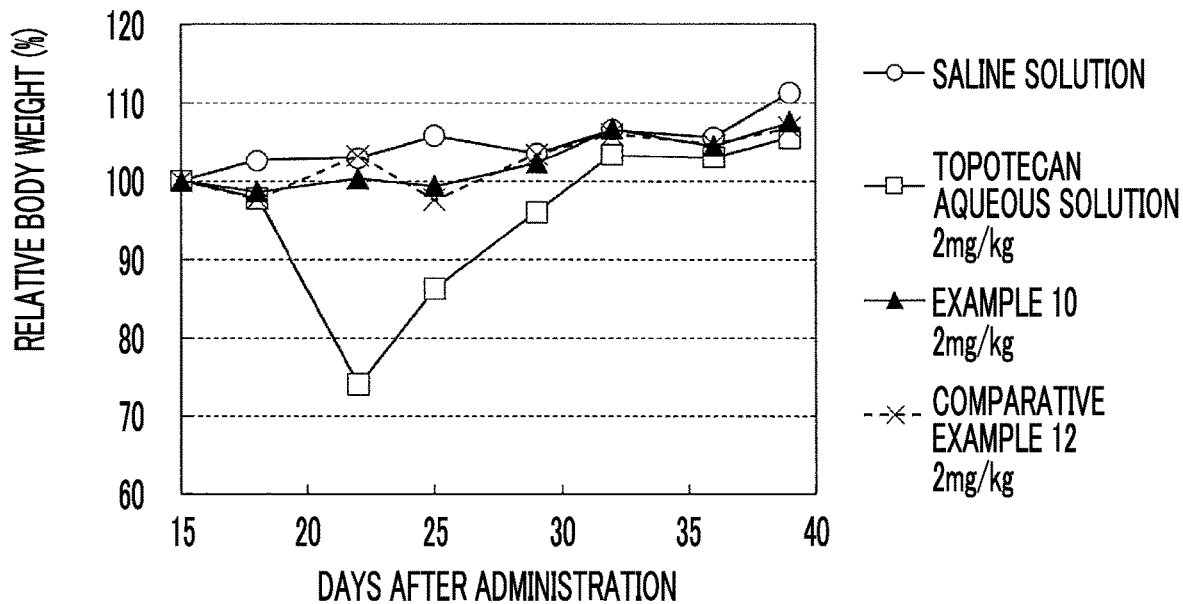
FIG. 1 shows the measurement results of body weight in a drug efficacy test using an A549 subcutaneous transplantation mouse model.

The numerical range indicated by using "to" in the present specification means a range including the numerical values described before and after "to" as the minimum value and the maximum value, respectively.

In referring herein to a content of a component in a composition, in a case where plural substances exist corresponding to a component in the composition, the content means, unless otherwise specified, the total amount of the plural substances existing in the composition.

The term "retention in blood" means a property in which a drug in a state of being encapsulated in a liposome is present in blood in a subject to which a liposome composition has been administered.

The "average particle size of liposome" means a cumulant average particle size measured using a dynamic light scattering method unless otherwise specified. Examples of commercially available measurement devices using dynamic light scattering include a concentrated system particle size analyzer FPAR-1000 (manufactured by Otsuka Electronics Co., Ltd.), a NANOTRAC UPA (manufactured by Nikkiso Co., Ltd.), and a NANOSIZER (manufactured by Malvern Panalytical Ltd.). It is also possible to calculate a volume average particle size and a number average particle size of the liposome by the conversion equation specific to the measurement device of each manufacturer.

In order to measure particles in the vicinity of 100 nm, the distribution of particles cannot be accurately captured by a static light scattering method or the like, and measurement by the dynamic light scattering method is preferable.

The term "insoluble particulates" is an item set by the regulatory authorities such as PMDA, FDA, and EMEA as safety and quality standards in medicinal compositions for systemic administration such as intravenous injection formulations. For example, in a case of evaluating a pharmaceutical composition by the first method (light shielding particle counting method) of Insoluble Particulate Test Method of the Japanese Pharmacopoeia <6.07> Injections in Japan, it is required that the number of insoluble particulates having a particle size of 10 μm or more contained in one drug vial of a product having a display volume of less than 100 mL is 6,000 or less and the number of insoluble particulates having a particle size of 25 μm or more is 600 or less. In addition, in a case of evaluating a pharmaceutical composition by the second method (microscopic particle counting method), it is required that the number of insoluble particulates having a particle size of 10 μm or more is 6,000 or less and the number of insoluble particulates having a particle size of 25 μm or more is 600 or less.

The insoluble particulates are defined only by the size of the particles, regardless of the components of the particles. For example, in the liposome composition, the insoluble particulates may be aggregates of liposomes themselves, aggregates and precipitates of the drug components leaked from the inside of the liposomes, or aggregates and precipitates of components of the liposome outer water phase. In particular, according to the description of JP2008-519045A and the like, it is known that the topotecan-encapsulated liposome in the present invention is a precipitate which is generated through the leakage of the encapsulated topotecan to the outside of the liposome, followed by decomposition into a less soluble degradant.

As a method of measuring insoluble particulates, there are, for example, a light shielding particle counting method which carries out optical detection of insoluble particulates (a particle counter, for example, HIAC 9703+ from Beckman Coulter, Inc. or Accusizer A2000 USP from Particle Sizing Systems, Inc. is used), and a microscopic particle counting method which visually observes a magnified image with a microscope and counts insoluble particulates.

In a case of a liposome pharmaceutical composition, particularly in a case of an injectable formulation, it is preferable that, as defined in Insoluble Particulate Test Method of the Japanese Pharmacopoeia <6.07> Injections, the number of particles having a particle size of more than 10 μm, which are contained in the pharmaceutical composition at the time of use, is 6000 or less and the number of particles having a particle size of more than 25 μm is 600 or less.

In the injectable formulation of the liposome pharmaceutical composition, the cause of the formation of insoluble particulates is considered to be attributable mostly to aggregation, coalescence, and degradation of liposome particle components that occur during storage, but is not limited thereto. Insoluble particulates tend to be generated depending on the amount of lipid which is a main material constituting the liposome. For example, in a case of considering a pharmaceutical composition containing 2 mL of a liposome composition having a lipid concentration of 20 mmol/L and then in a case where the number of particles having a particle size of more than 10 μm is 150 or less and the number of particles having a particle size of more than 25 μm is 15 or less per 1 μmol of lipid, it is possible to satisfy the condition that the number of particles having a particle size of more than 10 μm, which are contained in the pharmaceutical composition, is 6000 or less and the number of particles having a particle size of more than 25 μm is 600 or less, which is the standard defined in Insoluble Particulate Test Method of the Japanese Pharmacopoeia <6.07> Injections.

Also in the liposome composition according to the embodiment of the present invention, it is preferable that the number of particles having a particle size of more than 10 μm is 150 or less and the number of particles having a particle size of more than 25 μm is 15 or less per 1 μmol of lipid after storage for 1 month at 5° C. It is more preferable that the number of particles having a particle size of more than 10 μm is 75 or less and the number of particles having a particle size of more than 25 μm is 7.5 or less per 1 μmol of lipid after storage for 1 month at 5° C. It is still more preferable that the number of particles having a particle size of more than 10 μm is 25 or less and the number of particles having a particle size of more than 25 μm is 2.5 or less per 1 μmol of lipid after storage for 1 month at 5° C.

In addition, coarse particles having a particle size of more than 10 μm often increase due to deterioration with time during storage, and it is preferable to satisfy the above number of particles even after storage for 3 months and it is more preferable to satisfy the above number of particles even after storage for 1 year.

The "subject" is a mammal such as a human, a mouse, a monkey, or a domestic animal in need of the prevention or treatment of a disease or the like, and preferably a human in need of the prevention or treatment of a disease or the like.

Hereinafter, the present invention will be described in detail.

The liposome composition according to the first embodiment of the present invention is a liposome composition including a hydrophilic polymer-modified diacylphosphatidylethanolamine, a dihydrosphingomyelin, and cholesterols as components of a liposome membrane, in which the liposome composition encapsulates a drug, an inner water phase thereof contains ammonium sulfate, and a molar ratio of sulfate ions in the inner water phase to the drug in the entire water phase is 0.36 or more.

In addition, the liposome composition according to the second embodiment of the present invention is a liposome composition including a hydrophilic polymer-modified diacylphosphatidylethanolamine, a dihydrosphingomyelin, and cholesterols as components of a liposome membrane, in which the liposome composition encapsulates a drug, an inner water phase thereof contains ammonium sulfate, and the dihydrosphingomyelin is a dihydrosphingomyelin containing a long-chain alkyl group having 16 carbon atoms and a long-chain alkyl group having 18 carbon atoms.

In the present invention, retention of the liposome in blood is improved by using a hydrophilic polymer-modified diacylphosphatidylethanolamine, a dihydrosphingomyelin, and cholesterols as components of the liposome membrane. Further, inclusion of ammonium sulfate in the inner water phase suppresses the leakage of the drug from the liposome in blood and therefore improves an AUC. Further, by setting the molar ratio of sulfate ions in the inner water phase to the drug in the entire water phase to be 0.36 or more, the leakage of the drug from the liposome in blood is further suppressed and therefore a higher AUC is achieved.

As a result of the above, leakage of the drug from the inner water phase to the outer water phase can be suppressed even during cold storage, and the generation of insoluble particulates can be suppressed even under neutral conditions. That is, in the liposome composition according to the embodiment of the present invention, the pH of the outer water phase can be set to near neutrality (pH 7.4), and it became possible to use the "hydrophilic polymer-modified diacylphosphatidylethanolamine" hydrolyzing under acidic conditions for improving retention of liposomes in blood.

(Liposome)

The liposome is a closed vesicular body formed of a lipid bilayer membrane using lipids, and has a water phase (inner water phase) within the space of the closed vesicle. The inner water phase contains water and the like. The liposome is usually present in a state of being dispersed in an aqueous solution (outer water phase) outside the closed vesicle. The liposome may be single lamellar (which is also referred to as monolayer lamellar or unilamellar, and is a structure having a single bilayer membrane) or multilayered lamellar (which is also referred to as multilamellar and is an onion-like structure having multiple bilayer membranes where individual layers are compartmented by aqueous layers). In the present invention, a single lamellar liposome is preferred from the viewpoint of safety and stability in pharmaceutical applications.

The liposome is not particularly limited in terms of form thereof as long as it is a liposome capable of encapsulating a drug. The "encapsulating" means taking a form in which a drug is contained in an inner water phase and a membrane itself with respect to the liposome. For example, the liposome may be a form where a drug is encapsulated within a closed space formed of a membrane, a form where a drug is encapsulated in the membrane itself, or a combination thereof.

The average particle size of the liposome is generally 10 nm to 1000 nm, preferably 20 nm to 500 nm, more preferably 30 to 300 nm, still more preferably 30 nm to 200 nm, even more preferably 150 nm or less, for example, 30 nm to 150 nm, and particularly preferably 70 to 150 nm.

The liposome preferably has a spherical shape or a morphology close thereto.

The components that make up the lipid bilayer of the liposome are selected from lipids. As the lipids, those which can be dissolved in a mixed solvent of a water-soluble organic solvent and an ester-based organic solvent can be used.

The liposome in the present invention contains a hydrophilic polymer-modified diacylphosphatidylethanolamine, dihydrosphingomyelin, and cholesterols as components of the liposome membrane.

phosphatidic acid, phosphatidylcholine, phosphatidyl ethanolamine, phosphatidyl serine, phosphatidyl inositol, sphingomyelin, and cardiolipin, and hydrogenated products thereof (for example, hydrogenated soybean phosphatidylcholine (HSPC)).

In the present invention, dihydrosphingomyelin, which is a phospholipid having two acyl chains, is used as a lipid to be a base material for forming a lipid bilayer membrane.

By using dihydrosphingomyelin, retention of liposomes in blood can be improved.

By using dihydrosphingomyelin as a base material of the liposome membrane, it is possible to improve the partition properties of the liposome membrane to prevent the leakage of the encapsulated drug. It is speculated that this is because amide bonds of dihydrosphingomyelin have strong hydrogen bonding ability and can form a strong and highly partitionable membrane by strongly interacting with each other. In addition, amide bonds of dihydrosphingomyelin strongly interact with hydroxyl groups of cholesterol used simultaneously in the present invention, whereby a membrane having high partition properties can be formed. This is a function that cannot be achieved with commonly used lipids such as HSPC and lecithin having ester bonds.

In addition, since completely saturated dihydrosphingomyelin has a higher melting point and a lower mobility of the formed membrane relative to sphingomyelin having amide bonds but having unsaturated bonds in the acyl chain, it is speculated that dihydrosphingomyelin can form a membrane with higher partition properties relative to sphingomyelin.

Dihydrosphingomyelin generally has two long-chain alkyl groups in the molecule and examples of the dihydrosphingomyelin having two long-chain alkyl groups include dihydrosphingomyelin having two long-chain alkyl groups having 16 carbon atoms, dihydrosphingomyelin having a long-chain alkyl groups having 16 carbon atoms and a long-chain alkyl group having 18 carbon atoms, and dihydrosphingomyelin having a long-chain alkyl group having 16 carbon atoms and a long-chain alkyl group having 20 to 24 carbon atoms.

As dihydrosphingomyelin, it is preferable to use the following compound having a long-chain alkyl group having 16 carbon atoms and a long-chain alkyl group having 18 carbon atoms, in terms of prevention of drug leakage from liposomes. This is because the melting point becomes higher as the number of carbon atoms is larger, and therefore a liposome membrane having high partition properties can be formed.

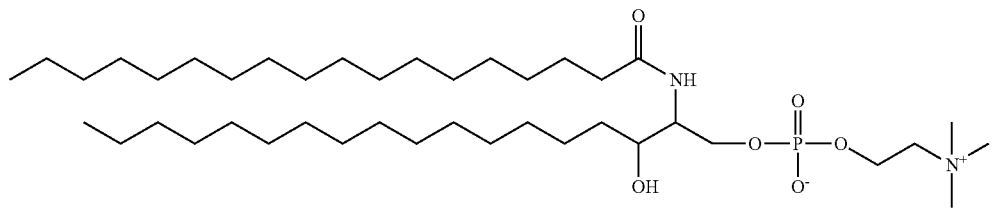 [SMILES: CCCCCCCCCCCCCCCCCC(=O)NC(COP(=O)([O-])OCC[N+](C)(C)C)C(O)CCCCCCCCCCCCCCC]

The liposome is a closed vesicular body formed of a lipid bilayer membrane using the lipids as described above, and in general, the lipids as a base material for forming the lipid bilayer membrane include phospholipids having two acyl chains, for example, natural or synthetic phospholipids such as phosphatidylcholine (lecithin), phosphatidyl glycerol, As dihydrosphingomyelin, for example, dihydrosphingomyelin obtained by reducing naturally occurring sphingomyelin by a general method may be used, or dihydrosphingomyelin obtained by synthesis may be used.

Generally, since most dihydrosphingomyelins derived from natural products such as chicken eggs generally have two long-chain alkyl groups having 16 carbon atoms, it is preferable to use dihydrosphingomyelin obtained by chemical synthesis, from the viewpoint that dihydrosphingomyelin having a long-chain alkyl group having 16 carbon atoms and a long-chain alkyl group having 18 carbon atoms can be obtained with high purity.

The percentage of dihydrosphingomyelin in the components of the liposome membrane (the total lipids constituting the liposome) is preferably 30 to 80 mol %, more preferably 40 to 70 mol %, and still more preferably 50 to 60 mol %.

Examples of the hydrophilic polymer in the hydrophilic polymer-modified diacylphosphatidylethanolamine include polyethylene glycols, polyglycerins, polypropylene glycols, polyvinyl alcohols, styrene-maleic acid anhydride alternating copolymers, polyvinylpyrrolidones, and synthetic polyamino acids. The above-mentioned hydrophilic polymers may be used alone or in combination of two or more thereof.

Among these, from the viewpoint of retention in blood of a composition, preferred are polyethylene glycols, polyglycerins, and polypropylene glycols are preferable, and polyethylene glycol (PEG), polyglycerin (PG), polypropylene glycol (PPG), and derivatives thereof are more preferable.

Polyethylene glycol (PEG) and derivatives thereof are still more preferable from the viewpoint of versatility and retention in blood.

Examples of derivatives of polyethylene glycol (PEG) include methoxy polyethylene glycols with no particular limitation.

The molecular weight of polyethylene glycols is not particularly limited, but it is 500 to 10,000 daltons, preferably 1,000 to 7,000 daltons, and more preferably 2,000 to 5,000 daltons.

The number of carbon atoms in the acyl moiety of diacylphosphatidylethanolamine is preferably 16 or more, for example, preferably 16 or more and 30 or less, more preferably 16 or more and 24 or less, and still more preferably 20.

Examples of the polyethylene glycol-modified diacylphosphatidylethanolamine include 1,2-distearoyl-3-phosphatidylethanolamine polyethylene glycols such as 1,2-distearoyl-3-phosphatidylethanolamine-PEG2000 (manufactured by Nippon Oil & Fats Co., Ltd.), 1,2-distearoyl-3-phosphatidylethanolamine-PEG5000 (manufactured by Nippon Oil & Fats Co., Ltd.), and distearoyl glycerol-PEG2000 (manufactured by Nippon Oil & Fats Co., Ltd.).

The percentage of the hydrophilic polymer-modified diacylphosphatidylethanolamine in the components of the liposome membrane (the total lipids constituting the liposome) is preferably 1 to 15 mol % and more preferably 2 to 10 mol %.

Examples of cholesterols include cholesterol which contains cyclopentahydrophenanthrene as a basic skeleton and in which carbon atoms are partially or completely hydrogenated and derivatives thereof. For example, cholesterol is preferable. In a case where the average particle size of the liposome decreases to 100 nm or less, the curvature of the lipid membrane becomes higher. The deformation of the membrane arranged in the liposome also becomes larger. It is effective to add cholesterol or the like in order to fill the deformation of the membrane caused by lipid (membrane-stabilizing effect).

In connection with the liposome, the addition of cholesterol is expected to lower the fluidity of the membrane of the liposome, for example, by filling the gaps in the membrane of the liposome.

The percentage of cholesterol in the components of the liposome membrane (lipids constituting the liposome) is preferably 20 mol % to 50 mol %, more preferably 30 mol % to 45 mol %, and still more preferably 35 mol % to 43 mol %.

In addition to the foregoing components, a hydrophilic polymer or the like for improving retention in blood, fatty acid, diacetyl phosphate, or the like as a membrane structure stabilizer, or α-tocopherol or the like as an antioxidant may be added to the liposome. In the present invention, it is preferable not to use an additive such as a dispersion aid which is not recognized for use in intravenous injection in medical use, for example, a surfactant.

(Drug)

The liposome composition according to the embodiment of the present invention contains a drug.

The type of drug is not particularly limited, but the anticancer agents exemplified below can be used. Specific examples of the anticancer agent include:

anthracycline-based anticancer agents such as doxorubicin, daunorubicin, and epirubicin;

cisplatin-based anticancer agents such as cisplatin and oxaliplatin;

taxane-based anticancer agents such as paclitaxel and docetaxel;

vinca alkaloid-based anticancer agents such as vincristine and vinblastine;

bleomycin-based anticancer agents such as bleomycin;

sirolimus-based anticancer agents such as sirolimus;

camptothecin-based anticancer agents such as topotecan (also referred to as nogitecan), irinotecan, karenitecin (registered trademark) (also referred to as BNP1350), exatecan, lurtotecan, gimatecan (also referred to as ST1481), and verotecan (also referred to as CKD602);

metabolic antagonists such as methotrexate, fluorouracil, gemcitabine, cytarabine, and pemetrexed; and molecularly targeted drugs such as imatinib (Gleevec (registered trademark)), everolimus (Afinitol®), erlotinib (Tarceva (registered trademark)), gefitinib (Iressa (registered trademark)), sunitinib (Sutent (registered trademark)), sorafenib (Nexavar (registered trademark)), dasatinib (Splicel (registered trademark)), tamivarotene (Amnolake (registered trademark)), tretinoin (Besanoid (registered trademark)), bortezomib (Velcade (registered trademark)), and lapatinib (Tykerb (registered trademark)).

Among the foregoing drugs, topotecan (also referred to as nogitecan), doxorubicin, irinotecan, or sunitinib is preferable, and topotecan is more preferable.

The drug may be used in the form of a salt.

Examples of the salt of the drug include salts in a basic group such as amino group, a hydroxyl group, and an acidic group such as carboxyl group, which are commonly known in the art.

Examples of the salt in a basic group include salts with mineral acids such as hydrochloric acid, hydrobromic acid, phosphoric acid, boric acid, nitric acid, and sulfuric acid; salts with organic carboxylic acids such as formic acid, acetic acid, lactic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of the salt in an acid group include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-O-phenethylamine, 1-ephenamine, and N,N'-dibenzylethylenediamine.

The content of the drug in the liposome composition is not particularly limited, but is preferably 0.025 to 20 mg/ml and more preferably 0.25 to 10 mg/ml with respect to the liposome composition.

The amount of liposome-encapsulated drug relative to the liposome membrane-forming lipid is in a molar ratio of preferably 0.1 to 1.5 and more preferably 0.2 to 0.3 from the viewpoint of the release rate from the liposome, the osmotic pressure inside the liposome, and the liposome shape by the precipitated drug.

In a case where the molar ratio of the amount of drug to the lipid is too low, the area of the liposome membrane with respect to the unit drug amount is increased, the release rate of the drug from the liposome is increased, and therefore the function of improving the retention in blood is impaired. On the other hand, in a case where the molar ratio of the amount of drug to lipid is too high, the osmotic pressure inside the liposome is increased with an increased amount of the drug dissolved, thus resulting in destruction of the liposome, or in a case where the drug is precipitated inside the liposome, the precipitated solid grows large, thus resulting in deformation of the liposome shape.

(Ammonium Sulfate in Inner Water Phase)

The inner water phase of the liposome in the present invention contains ammonium sulfate. In the liposome composition which is the first embodiment of the present invention, the molar ratio of sulfate ions in the inner water phase to the drug in the entire water phase is 0.36 or more and preferably 0.4 or more. The molar ratio of sulfate ions in the inner water phase to the drug in the entire water phase is more preferably 0.4 or more and 1.8 or less and still more preferably 0.6 or more and 1.8 or less. By setting the molar ratio of sulfate ions in the inner water phase to the drug in the entire water phase as described above, it is possible to suppress leakage of the drug from the liposome in blood. In a case where the molar ratio of sulfate ions in the inner water phase to the drug in the entire water phase is too low, this leads to incomplete formation of a solid of the drug due to the sulfate, an increased concentration of the drug in dissolved state, which results in increased permeability of the liposome membrane in the liposome, and easy leakage of the drug from the liposome, so that the effect of improving retention in blood is impaired. In addition, in a case where the molar ratio of sulfate ions in the inner water phase to the drug in the entire water phase is too high, the osmotic pressure inside the liposome will be high, resulting in the destruction of the liposome structure, so the drug is likely to leak out of the liposome and therefore the effect of improving retention in blood is impaired.

In addition, in the present invention, the percentage of sulfate ions contained in the inner water phase of the liposome to sulfate ions in the entire liposome composition (ratio of sulfate ions in inner water phase) is preferably at least 80% and more preferably 90% or more, and simultaneously the percentage of the drug contained in the inner water phase of the liposome to the drug in the entire liposome composition (ratio of drug in inner water phase) is preferably at least 80% and more preferably 90% or more.

The drug concentration in the liposome can be measured, for example, by liquid chromatography/ultraviolet-visible absorbance detection. In addition, the sulfate ion concentration in the inner water phase of the liposome can be measured, for example, by ion chromatography.

(pH of Outer Water Phase)

The liposome composition according to the embodiment of the present invention can include a liposome encapsulating a drug, and an aqueous solvent (outer water phase) in which the liposome is dispersed. The outer water phase preferably has a neutral pH and specifically a pH of about 5.5 to 8.5.

In a case where drug leakage is extremely suppressed, drug leakage at the affected area, particularly at the tumor site, may also be suppressed, and therefore the desired efficacy may not be obtained.

The liposome composition according to the embodiment of the present invention has a surprising mechanism of suppressing drug leakage in blood, delivering a sufficient amount of drug to the tumor site, and rapidly releasing the drug in the tumor site.

The tumor site has the property that its ammonium concentration is higher than other organs such as blood (cited article: Nanomedicine: Nanotechnology, Biology, and Medicine, 11 (2015) 1841-1850). The liposome composition according to the embodiment of the present invention exhibits greatly increased drug release in an environment in which glutamine degradation is enhanced and therefore an ammonium concentration is high (5 mmol/L), like a tumor.

The liposome composition according to the embodiment of the present invention has a drug release rate of 20%/24 hours or less at 37° C. from liposomes in plasma having an ammonium concentration of 1 mmol/L or less and a drug release rate of 60%/24 hours or more at 37° C. from liposomes in plasma having an ammonium concentration of 4 to 6 mmol/L; and more preferably a drug release rate of 15%/24 hours or less at 37° C. from liposomes in plasma having an ammonium concentration of 1 mmol/L or less and a drug release rate of 70%/24 hours or more at 37° C. from liposomes in plasma having an ammonium concentration of 4 to 6 mmol/L.

(Method for Producing Liposome Composition)

The method for producing the liposome composition according to the embodiment of the present invention is not particularly limited. For example, the liposome composition according to the embodiment of the present invention can be produced by the following steps:

(a) preparation of an oil phase;
(b) preparation of a water phase;
(c) liposome particle formation by emulsification;
(d) particle size regulation by extruder;
(e) replacement of liposome outer water phase liquid by dialysis;
(f) encapsulation of drug in liposome particles by remote loading; and
(g) removal of outer water phase drug by dialysis.

The particle size regulation by extruder (d) may or may not be carried out.

<(a) Preparation of Oil Phase>

(a) In preparation of an oil phase, individual components (hydrophilic polymer-modified diacylphosphatidylethanolamine, dihydrosphingomyelin, and cholesterols) constituting the liposome and an organic solvent are mixed, and the mixture is heated to dissolve the above-mentioned components, whereby an oil phase can be produced.

Although the organic solvent used in the oil phase is not particularly limited, for example, a water-soluble organic solvent which is optionally mixed with water can be used.

Examples of the water-soluble organic solvent include alcohols such as methanol, ethanol, n-propanol, isopropanol, n-butanol, isobutanol, and t-butanol; glycols such as glycerin, ethylene glycol, and propylene glycol; and polyalkylene glycols such as polyethylene glycol. Among these, alcohols are preferred. The alcohol is preferably at least one selected from ethanol, methanol, 2-propanol, or t-butanol, more preferably at least one selected from ethanol, 2-propanol, or t-butanol, and still more preferably ethanol.

The concentration of each component constituting the liposome is not particularly limited and can be appropriately adjusted.

<(b) Preparation of Water Phase>

Water (distilled water, water for injection, or the like), physiological saline, various buffer solutions or aqueous solutions of sugars (sucrose or the like), or mixtures thereof (aqueous solvent) can be used as the water phase. In the present invention, it is preferable to use an aqueous ammonium sulfate solution as the water phase, in a case where a drug is encapsulated in liposome particles by remote loading which will be described later.

The buffer solution is not limited to organic and inorganic buffer solutions, and a buffer solution having a buffering action in the vicinity of a pH close to that of the body fluid is suitably used and examples thereof include a phosphate buffer solution, a Tris buffer solution, a citrate buffer solution, an acetate buffer solution, and a Good's buffer solution. The inner water phase of the liposome may be an aqueous solution in which the liposomes are dispersed in a case of producing liposomes, or may be water, physiological saline, an aqueous solution of various buffer solutions or sugars, or a mixture thereof which is newly added. The water used as an outer water phase or an inner water phase is preferably free from impurities (dust, chemicals, or the like).

The physiological saline refers to an inorganic salt solution adjusted to be isotonic with the human body fluid, and may further have a buffering function. Examples of the physiological saline include saline containing 0.9 w/v % (mass/volume percent) of sodium chloride, PBS, and Tris buffered physiological saline.

In the present invention, the water phase includes both an outer water phase and an inner water phase.

The outer water phase in the present invention means an aqueous solution in which liposomes are dispersed. For example, in a case of an injection, a solution occupying the outside of the liposome of a dispersion liquid of liposomes packaged and stored in a vial or prefilled syringe becomes an outer water phase. Also, similarly for a liquid to be dispersed at the time of use in a case of being administered by means of an attached dispersion solution or other solutions, a solution occupying the outside of the liposome of a dispersion liquid of liposomes becomes an outer water phase.

The inner water phase in the present invention refers to a water phase in closed vesicles separated by lipid bilayer membranes of liposomes.

<(c) Liposome Particle Formation by Emulsification>

In the emulsifying step, an oil phase and a water phase are mixed to prepare an aqueous solution containing lipids, which can be then emulsified with stirring. An oil phase where lipid has been dissolved in an organic solvent and a water phase are mixed, stirred, and emulsified to thereby prepare an emulsion where the oil phase and the water phase are emulsified in an O/W type (oil-in-water type). After mixing, liposomes are formed by removing a portion or all of the organic solvent derived from the oil phase by evaporation. Alternatively, a portion or all of the organic solvent in the oil phase is evaporated in the course of the stirring-emulsification to form liposomes.

As a method of stirring, ultrasonic waves or mechanical shearing is used for particle miniaturization. In addition, extruder processing or microfluidizer processing of allowing to pass through a filter having a certain pore size can be carried out for uniformity of particle sizes. Use of an extruder or the like can result in decomposition of secondarily formed multivesicular liposomes into univesicular liposomes.

The emulsifying step is not limited as long as it is a step of emulsification, but it is preferably a step of applying a high shearing and performing microparticulation with an emulsifying step including an organic solvent. The high shear rate is defined in terms of peripheral speed of a stirring blade of an emulsification machine and is preferably 5 m/s to 32 m/s and particularly preferably 20 m/s to 30 m/s. If necessary, evaporation (desolvation) of the organic solvent used in the emulsifying step may be carried out to form liposomes.

The liquid temperature in the emulsifying step in a case of producing liposomes can be appropriately adjusted, but the liquid temperature at the time of mixing an oil phase and a water phase is preferably higher than or equal to a phase transition temperature of the lipid to be used. For example, in a case where a lipid having a phase transition temperature of 35° C. to 40° C. is used, the liquid temperature is preferably set to 35° C. to 70° C.

In the emulsifying step, the organic solvent and water may be evaporated from the aqueous solution containing liposomes. As to the evaporation referred to herein, a portion or all of the organic solvent derived from the oil phase and the water derived from the water phase may be forcibly removed as an evaporation step, or a portion or all of the organic solvent derived from the oil phase and the water derived from the water phase may evaporate naturally during the course of stirring-emulsification.

The method of evaporation is not particularly limited. For example, at least one of a step of heating to evaporate an organic solvent and water, a step of continuing the standing or slow stirring after emulsification, or a step of carrying out vacuum degassing may be carried out.

<(d) Particle Size Regulation by Extruder>

The obtained liposomes can be made uniform in particle size by using dialysis, filtration, extrusion processing, or the like.

The extrusion processing means a step of passing liposomes through a filter having a fine pore to apply a physical shearing, thereby carrying out microparticulation of the liposomes. In a case where the liposomes are passed through, rapid microparticulation thereof may be achieved by incubating the liposome dispersion liquid and the filter at a temperature higher than or equal to the phase transition temperature of the membrane constituting the liposome.

In addition, the particle size regulation by an extruder may or may not be carried out.

<(e) Replacement of Liposome Outer Water Phase Liquid by Dialysis>

In the present invention, in a case where the drug is encapsulated in the liposome particles by remote loading, the liposome outer water phase liquid may be replaced by dialysis. An aqueous solution of 0.05% to 5% by mass of NaCl can be used as a dialysis liquid which is not particularly limited. Dialysis of the liposome liquid using the above-mentioned dialysis liquid can provide liposomes in which ammonium sulfate present in the outer water phase is removed and the outer water phase is replaced with the dialysis liquid.

<(f) Encapsulation of Drug in Liposome Particles by Remote Loading Method>

In the present invention, it is preferable to encapsulate a drug in liposome particles by a remote loading method.

In the present invention, the remote loading method refers to a method of producing an empty liposome in which a drug is not encapsulated and then adding the drug to the liposome outer liquid to introduce the drug into the liposome. The method of remote loading is not particularly limited, but a method using an ammonium salt is preferable and a method using ammonium sulfate is more preferable.

In the remote loading method, the drug added to the outer liquid is actively transferred to liposomes and incorporated into the liposomes. A solubility gradient, an ion gradient, a pH gradient, or the like is used as the driving force. For example, there is a method of introducing a drug into liposomes using an ion gradient formed across a liposome membrane. For example, there is a technique of adding a drug into liposomes that are preformed by the remote loading method using a $Na^+/K^+$ concentration gradient.

Among the ion gradients, a proton concentration gradient is generally used. For example, there is an aspect in which the inner (inner water phase) pH of the liposome membrane has a pH gradient lower than the outer (outer water phase) pH. The pH gradient can be specifically formed by a concentration gradient of ammonium ion gradient or the like.

<(g) Removal of Outer Water Phase Drug by Dialysis>

The drug-encapsulated liposome liquid may be subjected to dialysis to remove the drug not contained in the liposomes. For example, by subjecting the drug-encapsulated liposome liquid to dialysis, using a predetermined concentration of sucrose/histidine buffer as a dialysis liquid, the drug present in the outer water phase can be removed to obtain a liposome composition in which the outer water phase is replaced with the dialysis liquid.

<Sterile Filtration>

The liposome composition obtained above is preferably subjected to sterile filtration. Regarding the filtration method, it is possible to remove unwanted materials from an aqueous solution containing liposomes by using a hollow fiber membrane, a reverse osmosis membrane, a membrane filter, or the like. In the present invention, it is preferable to filter the liposome composition through a filter having a sterilizable pore size (preferably a 0.2 μm filtration sterilization filter).

To prevent an effect of deformation of liposomes on the average particle size, the sterile filtration step and the below-described aseptic filling step are preferably carried out at a temperature lower than or equal to the phase transition temperature of the lipid constituting the liposome. For example, in a case where the phase transition temperature of the lipid is around 50° C., the sterile filtration step and the below-described aseptic filling step are carried out at temperature of preferably about 0° C. to 40° C., and more specifically about 5° C. to 30° C.

<Aseptic Filling>

The liposome composition obtained after sterile filtration is preferably aseptically filled for medical applications. Known methods can be applied for aseptic filling. A liposome composition suitable for medical applications can be prepared by aseptically filling the liposome composition in a container.

(Pharmaceutical Composition)

In connection with the route of administration, the liposome composition according to the embodiment of the present invention may also contain at least one of a tonicity agent, a stabilizer, an antioxidant, or a pH adjusting agent which is pharmaceutically acceptable. That is, the liposome composition according to the embodiment of the present invention can be provided as a pharmaceutical composition.

The tonicity agent is not particularly limited and examples thereof include inorganic salts such as sodium chloride, potassium chloride, sodium hydrogen phosphate, sodium dihydrogen phosphate, and potassium dihydrogen phosphate; polyols such as glycerol, mannitol, and sorbitol; and sugars such as glucose, fructose, lactose, and sucrose.

The stabilizer is not particularly limited and examples thereof include sugars such as glycerol, mannitol, sorbitol, lactose, and sucrose.

The antioxidant is not particularly limited and examples thereof include ascorbic acid, uric acid, tocopherol homologues (for example, vitamin E, four tocopherol isomers α, β, γ, and δ), cysteine, and ethylenediaminetetraacetic acid (EDTA). Stabilizers and antioxidants may be respectively used alone or in combination of two or more thereof.

Examples of the pH adjusting agent include sodium hydroxide, citric acid, acetic acid, triethanolamine, sodium hydrogen phosphate, sodium dihydrogen phosphate, and potassium dihydrogen phosphate.

The liposome composition according to the embodiment of the present invention may contain an organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerol, propylene glycol, polyethylene glycol, vaseline, paraffin, stearyl alcohol, stearic acid, human serum albumin (HSA), mannitol, sorbitol, lactose, phosphate buffered saline (PBS), sodium chloride, sugars, a biodegradable polymer, a serum-free medium, each of which is pharmaceutically acceptable, or an additive which is acceptable as a pharmaceutical additive.

The container in which the liposome composition according to the embodiment of the present invention is filled is not particularly limited, and it is preferably made out of a material having low oxygen permeability. Examples of the container include a plastic container, a glass container, and a bag made out of a laminate film having an aluminium foil, an aluminium-deposited film, an aluminium oxide-deposited film, a silicon oxide-deposited film, a polyvinyl alcohol, an ethylene-vinyl alcohol copolymer, a polyethylene terephthalate, a polyethylene naphthalate, a polyvinylidene chloride, or the like as a gas barrier layer. If necessary, light may be shielded by adopting a bag or the like using a colored glass, an aluminium foil, an aluminium-deposited film, or the like.

In the container in which the liposome composition is filled, in order to prevent oxidation by oxygen present in the space of the container, it is preferable to replace the gases in the container space and drug solution with inert gases such as nitrogen. For example, an injection solution is bubbled with nitrogen, whereby the filling of the injection solution into a container can be carried out under a nitrogen atmosphere.

The administration route of the pharmaceutical composition according to the embodiment of the present invention is preferably parenteral administration. Examples of the parenteral administration include intravenous injection such as intravenous drip, intramuscular injection, intraperitoneal injection, subcutaneous injection, intraocular injection, and intrathecal injection. The administration method of the pharmaceutical composition may be, for example, administration by syringe or intravenous drip.

The dosage and frequency of administration of the pharmaceutical composition according to the embodiment of the present invention may be appropriately set depending on the type of drug, the condition of the patient, and the like. The dose of the pharmaceutical composition can be generally set in the range of 0.01 mg/kg/day to 100 mg/kg/day in terms of the amount of drug which is an active ingredient. The dose of the pharmaceutical composition can be set in the range of 2 mg to 10 mg per dose in terms of the amount of drug which is an active ingredient, but it is not limited to these dosages.

The pharmaceutical composition according to the embodiment of the present invention can be preferably used as an anticancer agent.

The type of cancer to which the pharmaceutical composition according to the embodiment of the present invention is applied is not particularly limited, and examples thereof include lung cancer (especially small cell lung cancer), ovarian cancer, pediatric solid tumor, uterine cervical cancer, breast cancer, prostate cancer, endometrial cancer, gastric cancer (gastric adenocarcinoma), non-small cell lung cancer, pancreatic cancer, cervical squamous cell carcinoma, esophageal cancer, bladder cancer, melanoma, colon cancer, renal cell cancer, non-Hodgkin's lymphoma, urothelial cancer, multiple myeloma, acute myeloid leukemia, chronic myeloid leukemia, acute lymphocytic leukemia, adult T cell leukemia, bone marrow metastatic cancer, sarcoma, soft tissue tumor, chronic myelomonocytic leukemia, Hodgkin's lymphoma, and cutaneous T cell lymphoma.

EXAMPLES

Hereinafter, the present invention will be described in detail with reference to Examples. However, the present invention is not limited to the Examples.

SM represents sphingomyelin (COATSOME NM-10, manufactured by NOF Corporation).

Chicken egg-derived DHSM represents dihydrosphingomyelin obtained by hydrogenating chicken egg-derived SM (synthetic product obtained by hydrogenating COATSOME NM-10 (manufactured by NOF Corporation)). This chicken egg-derived DHSM is a mixture containing DHSM having two alkyl chains having 16 carbon atoms, which accounts for 70% to 80% of a total of the chicken egg-derived DHSM, and DHSM having different alkyl chain lengths, which is the remainder.

Totally synthetic DHSM represents dihydrosphingomyelin produced by chemical synthesis so as to contain 98% or more of the following compound having a long-chain alkyl group having 16 carbon atoms and a long-chain alkyl group having 18 carbon atoms.

SUNBRIGHT DSPE-020CN (hereinafter referred to as DSPE-PEG, manufactured by NOF Corporation) was used as PEG phospholipid (denoted as PEG in the table).

Cholesterol HP (manufactured by Nippon Fine Chemical Co., Ltd.) was used as cholesterol (denoted as Chol in the table).

Comparative Examples 1 to 10

(a) Preparation of Oil Phase

For Comparative Example 1, 11.52 g of SM, 4.3 g of PEG phospholipid, and 4.32 g of cholesterol were respectively weighed. For Comparative Examples 2 to 10, the amounts of SM or chicken egg-derived DHSM, PEG phospholipid, and cholesterol were changed to the ratios described in Table 1. The lipid was mixed with 381 mL of ethanol and dissolved at 65° C. to prepare an oil phase.

(b1) Preparation of Water Phase 1

25.2 g of ammonium sulfate was dissolved in 1118.5 g of water to prepare water phase 1.

(b2) Preparation of Water Phase 2

5.04 g of ammonium sulfate was dissolved in 223.7 g of water to prepare water phase 2.

(c) Liposome Particle Formation by Emulsification

The water phase 1 prepared in (b1) was heated to 65° C., the whole of the oil phase prepared in (a) was added thereto, and then these phases were mixed with a precision emulsification disperser at a peripheral speed of 26 m/s for 60 minutes. Subsequently, the water phase 2 at room temperature was added thereto, followed by continuing the stirring at a peripheral speed of 0.1 m/s while heating at 65° C. to evaporate the organic solvent and water. In a case where the liquid was concentrated to 600 mL, heating and stirring were stopped and therefore evaporation was terminated.

(e) Replacement of Liposome Outer Water Phase Liquid by Dialysis

An aqueous solution of 3.15% by mass NaCl was used as a dialysis liquid. Using this dialysis liquid, the liquid obtained in (c) was subjected to cross-flow filtration at room temperature to remove ammonium sulfate present in the outer water phase to obtain liposomes in which the outer water phase was replaced with the dialysis liquid.

(f) Encapsulation of Topotecan in Liposome Particles by Remote Loading

Water for injection was added to topotecan hydrochloride (manufactured by Biocompounds Pharmaceutical Inc.) to 5 mg/mL. Further, while stirring the liquid well, an 8 mol/L HCl solution was added to adjust the pH to about 3 to dissolve topotecan. Liposomes were added to the resulting topotecan solution at a volume ratio of 1/1, followed by heating at 60° C. for 60 minutes.

(g) Removal of Outer Water Phase Topotecan by Dialysis

A sucrose/histidine buffer consisting of 9.4% by mass sucrose and 10 mmol/L histidine was prepared as a dialysis liquid. Using this dialysis liquid, the liquid obtained in (f) was subjected to cross-flow filtration at room temperature to

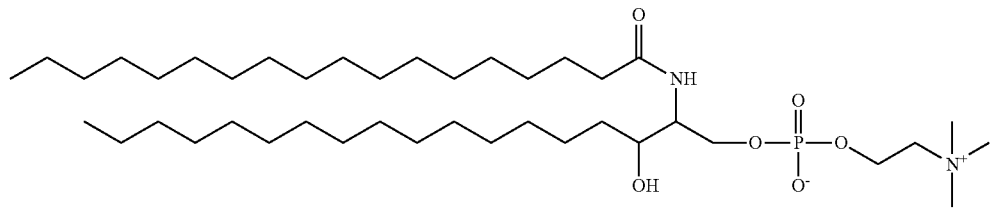 [SMILES: CCCCCCCCCCCCCCCCCC(=O)NC(COP(=O)([O-])OCC[N+](C)(C)C)C(O)CCCCCCCCCCCCCCC]

remove topotecan present in the outer water phase to obtain topotecan-containing liposomes in which the outer water phase was replaced with the dialysis liquid.

Comparative Examples 11 and 12

(a) Preparation of Oil Phase

For Comparative Example 11, 0.517 g of chicken egg-derived DHSM and 0.233 g of cholesterol were respectively weighed. For Comparative Example 12, the amounts of SM and cholesterol were changed to the ratios described in Table 1. In order to label liposomes with DiI (1,1'-dioctadecyl-3, 3,3',3'-tetramethylindocarbocyanine perchlorate), an amount of DiI, which was 0.2 mol % with respect to total lipids, was weighed and dissolved in ethanol. Ethanol was added to the DiI ethanol solution to make a total volume of 1.5 mL. The weighed lipid and this organic solvent were mixed and heated to 65° C. to dissolve the lipid, thus preparing an oil phase.

(b) Preparation of Water Phase 0.9 g of ammonium sulfate and 2.16 g of sucrose were dissolved in 13.5 g of water to prepare a water phase.

(c) Liposome Particle Formation by Mixing Oil Phase and Water Phase

The water phase prepared in (b) was heated to 65° C. and stirred with a magnetic stirrer (3000 rpm). The whole oil phase prepared in (a) was heated to 65° C. with a hot plate, and the whole oil phase was sucked with a syringe and heated for 5 minutes with a hot plate. The oil phase was added dropwise over 30 seconds to the heated water phase.

(d) Particle Size Regulation by Extruder

The liquid obtained in (c) was subjected to the particle size regulation by sequentially passing it through a filter using an extruder (Mini Extruder, manufactured by Avanti Polar Lipids, Inc.) under heating at 70° C.

(e) Replacement of Liposome Outer Water Phase Liquid by Dialysis

An aqueous solution of 0.09% by mass of NaCl was used as a dialysis liquid. Using this dialysis liquid, the liquid obtained in (c) or (d) was subjected to dialysis at room temperature to remove ammonium sulfate present in the outer water phase to obtain liposomes in which the outer water phase was replaced with the dialysis liquid.

(f) Encapsulation of Topotecan in Liposome Particles by Remote Loading

Water for injection was added to topotecan hydrochloride (manufactured by Biocompounds Pharmaceutical Inc.) to 5 mg/mL. Further, while stirring the liquid well, an 8 mol/L HCl solution was added to adjust the pH to about 3 to dissolve topotecan. Liposomes were added to the resulting topotecan solution at a volume ratio of 1/1, followed by heating at 60° C. for 120 minutes.

(g) Removal of Outer Water Phase Topotecan by Dialysis

A sucrose/histidine buffer consisting of 9.4% by mass sucrose and 10 mmol/L histidine was prepared as a dialysis liquid. Using this dialysis liquid, the liquid obtained in (f) was subjected to dialysis at room temperature to remove topotecan present in the outer water phase to obtain topotecan-containing liposomes in which the outer water phase was replaced with the dialysis liquid.

Examples 1 to 8

(a) Preparation of Oil Phase

For Example 1, 11.52 g of chicken egg-derived DHSM, 4.32 g of PEG phospholipid (SUNBRIGHT DSPE-020CN, manufactured by NOF Corporation, hereinafter referred to as DSPE-PEG), and 4.32 g of cholesterol were respectively weighed. For Examples 2 to 8, the amounts of DHSM, DSPE-PEG, and cholesterol were changed to the ratios described in Table 2. The lipid was mixed with 381 mL of ethanol and dissolved at 65° C. to prepare an oil phase.

(b1) Preparation of Water Phase 1

25.2 g of ammonium sulfate was dissolved in 1118.5 g of water to prepare water phase 1.

(b2) Preparation of Water Phase 2

5.04 g of ammonium sulfate was dissolved in 223.7 g of water to prepare water phase 2.

(c) Liposome Particle Formation by Emulsification

The water phase 1 prepared in (b1) was heated to 65° C., the whole of the oil phase prepared in (a) was added thereto, and then these phases were mixed with a precision emulsification disperser at a peripheral speed of 26 m/s for 60 minutes. Subsequently, the water phase 2 at room temperature was added thereto, followed by continuing stirring at a peripheral speed of 0.1 m/s while heating at 65° C. to evaporate the organic solvent and water. Heating and stirring were stopped in a case where the liquid was concentrated to 600 mL and therefore evaporation was stopped.

(e) Replacement of Liposome Outer Water Phase Liquid by Dialysis

An aqueous solution of 3.15% by mass NaCl was used as a dialysis liquid. Using this dialysis liquid, the liquid obtained in (c) was subjected to cross-flow filtration at room temperature to remove ammonium sulfate present in the outer water phase to obtain liposomes in which the outer water phase was replaced with the dialysis liquid.

(f) Encapsulation of Topotecan in Liposome Particles by Remote Loading

Water for injection was added to topotecan hydrochloride (manufactured by Biocompounds Pharmaceutical Inc.) to 5 mg/mL. Further, while stirring the liquid well, an 8 mol/L HCl solution was added to adjust the pH to about 3 to dissolve topotecan. Liposomes were added to the resulting topotecan solution at a volume ratio of 1/1, followed by heating at 60° C. for 60 minutes.

(g) Removal of Outer Water Phase Topotecan by Dialysis

A sucrose/histidine buffer consisting of 9.4% by mass sucrose and 10 mmol/L histidine was prepared as a dialysis liquid. Using this dialysis liquid, the liquid obtained in (f) was subjected to cross-flow filtration at room temperature to remove topotecan present in the outer water phase to obtain topotecan-containing liposomes in which the outer water phase was replaced with the dialysis liquid.

Examples 9 and 10

(a) Preparation of Oil Phase

For Example 9, 0.412 g of chicken egg-derived DHSM, 0.153 g of DSPE-PEG, and 0.153 g of cholesterol were respectively weighed. For Example 10, the amounts of chicken egg-derived DHSM, DSPE-PEG, and cholesterol were changed to the ratios described in Table 2. In order to label liposomes with DiI, an amount of DiI, which was 0.2 mol % with respect to total lipids, was weighed and dissolved in ethanol. Ethanol was added to the resulting DiI ethanol solution to make a total volume of 11.25 mL, and 3.75 mL of ethyl acetate was further added thereto. The weighed lipid and this organic solvent were mixed and heated to 60° C. to dissolve the lipid, thus preparing an oil phase.

(b) Preparation of Water Phase 0.9 g of ammonium sulfate was dissolved in 40 g of water to prepare a water phase.

(c) Liposome Particle Formation by Emulsification

The water phase prepared in (b) was heated to 70° C., the whole of the oil phase prepared in (a) was added thereto (volume ratio: water phase/oil phase=8/3), and then these phases were mixed using an emulsification machine (Excel Auto homogenizer ED-3, manufactured by Nippon Seiki Seisakusho Co., Ltd.) at 3000 rpm (rotation per minute: $\frac{1}{60}$ s$^{-1}$) for 30 minutes. This was followed by continuing the stirring at 300 rpm while heating at 65° C. to evaporate the organic solvent and water. In a case where the liquid was concentrated to 15 g, the heating and stirring were stopped and therefore the evaporation was terminated.

(d) Particle Size Regulation by Extruder

The liquid obtained in (c) was subjected to the particle size regulation by sequentially passing it through a filter using an extruder (Mini Extruder, manufactured by Avanti Polar Lipids, Inc.) under heating at 70° C.

(e) Replacement of Liposome Outer Water Phase Liquid by Dialysis

An aqueous solution of 0.09% by mass of NaCl was used as a dialysis liquid. Using this dialysis liquid, the liquid obtained in (c) or (d) was subjected to dialysis at room temperature to remove ammonium sulfate present in the outer water phase to obtain liposomes in which the outer water phase was replaced with the dialysis liquid.

(f) Encapsulation of Topotecan in Liposome Particles by Remote Loading

Water for injection was added to topotecan hydrochloride (manufactured by Biocompounds Pharmaceutical Inc.) to 5 mg/mL. Further, while stirring the liquid well, an 8 mol/L HCl solution was added to adjust the pH to about 3 to dissolve topotecan. Liposomes were added to the resulting topotecan solution at a volume ratio of 1/1, followed by heating at 60° C. for 120 minutes.

(g) Removal of Outer Water Phase Topotecan by Dialysis

A sucrose/histidine buffer consisting of 9.4% by mass sucrose and 10 mmol/L histidine was prepared as a dialysis liquid. Using this dialysis liquid, the liquid obtained in (f) was subjected to dialysis at room temperature to remove topotecan present in the outer water phase to obtain topotecan-containing liposomes in which the outer water phase was replaced with the dialysis liquid.

[Measurement and Evaluation of Physical Properties]

<Average Particle Size>

In the present invention, the average particle size refers to a cumulant average particle size measured by a dynamic light scattering method. The average particle size in each of Examples and Comparative Examples described in table is a cumulant average particle size measured by a dynamic light scattering method using a concentrated system particle size analyzer FPAR-1000AS (manufactured by Otsuka Electronics Co., Ltd.) with an autosampler.

The measurement results are shown in Tables 1 and 2.

<Topotecan Concentration Measurement>

The sample was measured with a high performance liquid chromatography (HPLC) apparatus Nexera-i LC-2040C (manufactured by Shimadzu Corporation) to quantify the concentration of topotecan. The results are shown in Tables 1 and 2. The specific measurement method is as follows.

In the liposomes of Tables 1 and 2, the percentage of the drug contained in the inner water phase of the liposome to the drug in the entire liposome composition was at least 95%, except for Comparative Example 10 in which the percentage of the drug contained in the inner water phase of the liposome to the drug in the entire liposome composition was 59%.

Measurement of Topotecan Amount in Liposome Formulation

The prepared liposome liquid was dissolved in methanol and filtered to obtain a sample solution. Topotecan hydrochloride was diluted to prepare a calibration curve standard solution. Using the sample solution and the calibration curve standard solution thus prepared, the amount of topotecan in liposome formulation was measured by liquid chromatography/ultraviolet-visible absorbance detection.

The concentration of topotecan in the inner water phase was calculated by subtracting the concentration of topotecan in the outer water phase from the concentration of topotecan in the entire water phase. The concentration of topotecan in each water phase was measured as follows.

(Concentration of Topotecan in Entire Water Phase)

50 μL of the liposome dispersion liquid was measured and 950 μL of methanol was added thereto, followed by stirring with a vortex for 1 minute. 100 μL of the liquid was measured and 900 μL of Milli-Q water was added thereto, followed by stirring with a vortex for 1 minute to prepare an HPLC analysis sample.

(Concentration of Topotecan in Outer Water Phase)

50 μL of the liposome dispersion liquid was measured and then diluted by adding 450 μl of a 9.4 wt % sucrose/10 mM histidine aqueous solution. 200 μL of PBS was added to 100 μL of the diluted liquid which was then mixed by inversion. The dispersion liquid was ultracentrifuged (200,000 g, 20° C., 60 minutes), and the supernatant was used as an HPLC analysis sample. The ultracentrifugation was carried out using Hitachi himac CP80WX.

a) Preparation of Calibration Curve Standard Solution

About 20 mg of topotecan hydrochloride was weighed and dissolved in 20 mL of 10% by mass methanol aqueous solution. Milli-Q water was added to this liquid to prepare a solution having a topotecan hydrochloride concentration of 0.1, 1.0, 5.0, 10.0, 20.0, 50.0, or 100.0 ppm, which was then used as a calibration curve standard solution.

b) Preparation of Sample Solution (1) About 50 μL of a sample (liposome formulation solution) was weighed by MICROMAN (registered trademark), and about 950 μL of methanol weighed by MICROMAN was added thereto. After it was shaken for about 1 minute, the solution was visually confirmed to become clear.

(2) 100 μL of the solution of the above (1) was weighed by MICROMAN, and about 900 μL of Milli-Q water weighed by a micropipette was added thereto. This liquid was shaken for about 1 minute, sonicated for about 1 minute, and further shaken for about 10 seconds.

(3) The solution obtained by filtering the solution of the above (2) through a DISMIC (registered trademark) filter (pore diameter: 0.45 μm) was used as a sample solution.

c) Measurement

The measurement was carried out under the following conditions by liquid chromatography/UV-vis absorbance detection.

Measurement wavelength: 382 nm, column: Shiseido CAPCELLPAK C18 ACR 3 μm_3.0 mm*75 mm Column temperature: constant temperature of around 40° C.

Both of mobile phases A and B are a water/methanol/trifluoroacetic acid mixture, and feeding of the mobile phases was carried out by changing the mixing ratio of mobile phases A and B to control a concentration gradient.

Flow rate: 1.0 mL/minute, injection volume: 10 μL, autosampler temperature: constant temperature of around 25° C.

<Measurement of Sulfate Ion Concentration>

The sample was measured with an ion chromatography apparatus 883 Basic IC plus (manufactured by Metrohm AG) to quantify the concentration of sulfate ions. The results of measuring the molar ratio of sulfate ions to topotecan are shown in Tables 1 and 2. In the liposomes of Tables 1 and 2, the percentage of sulfate ions contained in the inner water phase of the liposome to sulfate ions in the entire liposome composition was at least 90%.

The concentration of sulfate ions in the inner water phase was calculated by subtracting the concentration of sulfate ions in the outer water phase from the concentration of sulfate ions in the entire water phase.

The concentration of sulfate ions in each water phase was measured as follows.

(Concentration of Sulfate Ions in Entire Water Phase)

50 μL of the liposome dispersion liquid was measured and 950 μL of methanol was added thereto, followed by mixing with ultrasonication for 15 seconds. 90 μL of the liquid was measured and 810 μL of water for injection (manufactured by Hikari Pharmaceutical Co., Ltd.) was added thereto, followed by mixing with ultrasonication for 30 seconds. 900 μL of ethyl acetate was added to the resulting solution which was then shaken well to extract lipids into an ethyl acetate phase. An appropriate amount of the water phase liquid was measured and used for ion chromatography analysis.

(Concentration of Sulfate Ions in Outer Water Phase)

100 μL of the liposome dispersion liquid was measured and then diluted by adding 900 μL of 5% glucose solution (manufactured by Otsuka Pharmaceutical Co., Ltd.). 450 μL of the resulting liquid was treated by ultrafiltration, and the filtrate was used as an ion chromatography analysis sample.

Centrifugation conditions were 7400 g, 5° C., and 30 minutes. The centrifuge used was Hitachi himac CF15RXII.

<Measurement of AUC>

The mice to which the prepared topotecan-containing liposomes were administered (dose: 1 mg/kg in terms of the amount of drug) were bled at 0.25, 2, 6, and 24 hours after administration. The blood was centrifuged at 800×g for 10 minutes to recover plasma. The concentration of topotecan was quantified for the collected plasma using liquid chromatography/mass spectrometry/mass spectrometry (LC/MS/MS). Using the pharmacokinetic analysis software WinNonlin (registered trademark) (available from Certara, L.P.), the area under blood concentration-time curve (AUC) up to infinite time after single administration was calculated from the transition of the topotecan concentration thus obtained. The unit of AUC is time×ng/mL (expressed as hr*ng/mL in the table). In addition, the AUC of the liposome described in [AACR-EORTC International Conference, San Francisco, Calif., Oct. 22-26, 2007, #C113 A Pharmacokinetics Study of a Novel Sphingomyelin/Cholesterol Liposomal Topotecan and Non-Liposomal Topotecan in Rats, William C. Zamboni et al.] is calculated to be 68152 hours×ng/mL.

TABLE 11

| | Average particle size | Concentration of topotecan in entire water phase | $SO_4^{2-}$ in inner water phase/topotecan in entire water phase | Molar ratio of components of liposome membrane | | | | Dose | AUC | Percentage of topotecan in inner water phase | Percentage of $SO_4^{2-}$ in inner water phase |
|---|---|---|---|---|---|---|---|---|---|---|---|
| | nm | ppm | mol/mol | PEG | Chol | DHSM | SM | mg/kg | hr*ng/mL | % | % |
| Comparative Example 1 | 101.7 | 2419 | 0.70 | 4.7% | 37% | 0% | 58% | 1.0 | 120189 | 99 | 100 |
| Comparative Example 2 | 96.3 | 2605 | 0.75 | 4.8% | 42% | 0% | 53% | 1.0 | 136669 | 100 | 100 |
| Comparative Example 3 | 90.2 | 2993 | 1.57 | 4.5% | 42% | 0% | 54% | 1.0 | 140108 | 100 | 98 |
| Comparative Example 4 | 105.2 | 2889 | 1.58 | 4.6% | 47% | 0% | 48% | 1.0 | 137082 | 100 | 98 |
| Comparative Example 5 | 91.1 | 2946 | 1.01 | 4.9% | 47% | 0% | 48% | 1.0 | 157878 | 100 | 96 |
| Comparative Example 6 | 99.3 | 2994 | 1.01 | 4.7% | 39% | 0% | 56% | 1.0 | 143615 | 100 | 100 |
| Comparative Example 7 | 101.2 | 3080 | 0.96 | 4.7% | 39% | 0% | 56% | 1.0 | 119518 | 100 | 98 |
| Comparative Example 8 | 100.8 | 2437 | 1.14 | 4.7% | 39% | 0% | 57% | 1.0 | 173179 | 100 | 98 |
| Comparative Example 9 | 90.8 | 1191 | 0.32 | 5.0% | 38% | 57% | 0% | 1.0 | 140277 | 100 | 100 |
| Comparative Example 10 | 131.2 | 1328 | 0.3 | 4.4% | 36% | 59% | 0% | 1.0 | 174087 | 59 | 100 |
| Comparative Example 11 | 106 | 1876 | — | 0% | 43% | 57% | 0% | 1.0 | 182694 | 99 | — |
| Comparative Example 12 | 111.2 | 2437 | — | 0% | 45% | 0% | 55% | 1.0 | 134591 | 100 | — |

TABLE 2

| | Average particle size | Concentration of topotecan in entire water phase | $SO_4^{2-}$ in inner water phase/ topotecan in entire water phase | Molar ratio of components of liposome membrane | | | | Dose | AUC | Percentage of topotecan in inner water phase | Percentage of $SO_4^{2-}$ in inner water phase |
|---|---|---|---|---|---|---|---|---|---|---|---|
| | nm | ppm | mol/mol | PEG | Chol | DHSM | SM | mg/kg | hr * ng/mL | % | % |
| Example 1 | 100 | 2160 | 0.66 | 5.6% | 40% | 54% | 0% | 1.0 | 227895 | 99 | 97 |
| Example 2 | 122 | 2347 | 1.38 | 5.3% | 39% | 56% | 0% | 1.0 | 201264 | 100 | 100 |

TABLE 2-continued

|  | Average particle size | Concentration of topotecan in entire water phase | $SO_4^{2-}$ in inner water phase/ topotecan in entire water phase | Molar ratio of components of liposome membrane | | | | Dose | AUC | Percentage of topotecan in inner water phase | Percentage of $SO_4^{2-}$ in inner water phase |
|---|---|---|---|---|---|---|---|---|---|---|---|
|  | nm | ppm | mol/mol | PEG | Chol | DHSM | SM | mg/kg | hr * ng/mL | % | % |
| Example 3 | 88 | 2353 | 1.16 | 5.4% | 38% | 56% | 0% | 1.0 | 270579 | 99 | 100 |
| Example 4 | 111.3 | 2167 | 1.05 | 5.2% | 38% | 57% | 0% | 1.0 | 295476 | 99 | 98 |
| Example 5 | 115.9 | 2659 | 0.8 | 5.1% | 35% | 60% | 0% | 1.0 | 330913 | 100 | 100 |
| Example 6 | 125.2 | 1349 | 0.9 | 4.4% | 36% | 60% | 0% | 1.0 | 261345 | 99 | 100 |
| Example 7 | 120.3 | 3984 | 0.6 | 5.0% | 43% | 52% | 0% | 1.0 | 278684 | 98 | 98 |
| Example 8 | 116.8 | 2254 | 1.1 | 5.1% | 43% | 52% | 0% | 1.0 | 307412 | 99 | 98 |
| Example 9 | 101 | 1561 | 0.73 | 10.0% | 40% | 50% | 0% | 1.0 | 245450 | 100 | 100 |
| Example 10 | 104 | 1758 | 0.68 | 5.1% | 40% | 55% | 0% | 1.0 | 270294 | 100 | 92 |

As can be seen from the results in Tables 1 and 2, in Examples 1 to 10 of the liposome composition including a hydrophilic polymer-modified diacylphosphatidylethanolamine, a dihydrosphingomyelin, and cholesterol as components of a liposome membrane, in which an inner water phase contains ammonium sulfate, and a molar ratio of sulfate ions in the inner water phase to the drug in the entire water phase is 0.36 or more, it was shown that the measured value of AUC is 200,000 or more and therefore high retention in blood can be achieved. On the other hand, in Comparative Examples 1 to 8 in which dihydrosphingomyelin is not used, Comparative Examples 9 and 10 in which the molar ratio of sulfate ions in the inner water phase to the drug in the entire water phase is less than 0.36, and Comparative Examples 11 and 12 in which hydrophilic polymer-modified diacylphosphatidylethanolamine is not used, it was shown that the measured value of AUC is less than 200,000, which is inferior to Examples 1 to 10.

<Drug Efficacy Test Using A549 Subcutaneous Transplantation Mouse Model>

Figure 2:
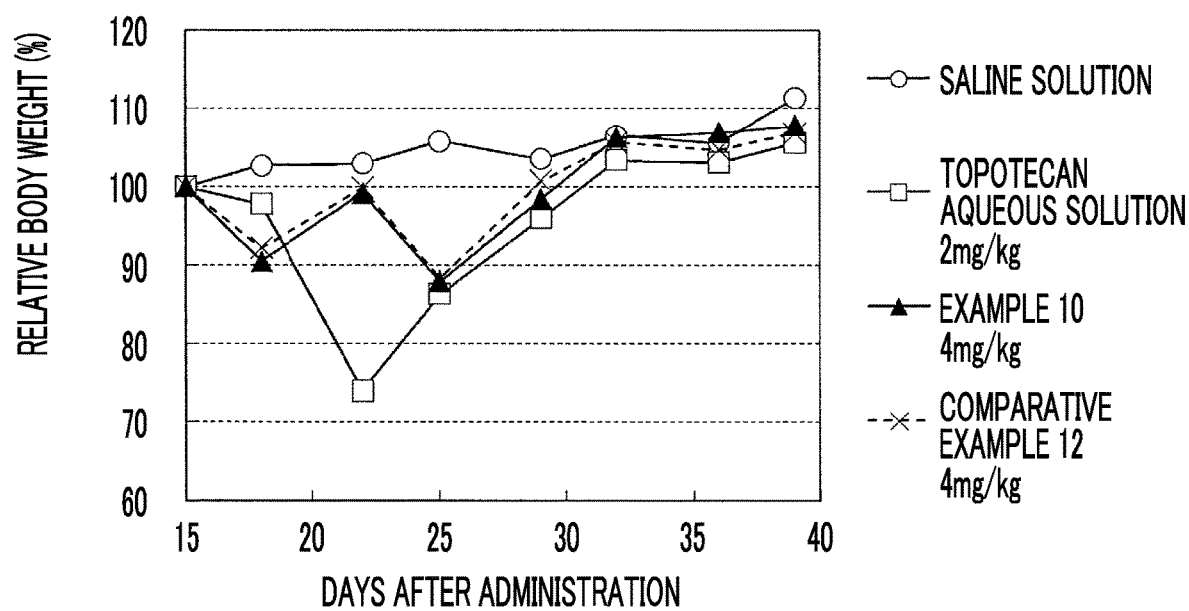
FIG. 2 shows the measurement results of body weight in a drug efficacy test using an A549 subcutaneous transplantation mouse model.

$1 \times 10^7$ A549 cells, a human lung cancer cell line, were subcutaneously transplanted in the right flank of Balb/c/nu/nu mice (female, 6-week old). From Day 15 after transplantation, the animals were administered the topotecan-containing liposomes prepared in Example 10 (4 mg/kg and 2 mg/kg in terms of the amount of drug, twice on a weekly basis), and the topotecan-containing liposomes prepared in Comparative Example 12 (4 mg/kg and 2 mg/kg in terms of the amount of drug, twice on a weekly basis). In addition, the animals were administered physiological saline as a negative control. In addition, the animals were administered a topotecan aqueous solution (2 mg/kg in terms of the amount of drug) as a comparative control. Body weight and tumor volume of the animals were measured twice weekly from the start of dosing. The measurement results of body weight are shown in FIGS. 1 and 2, and the measurement results of tumor volume are shown in FIGS. 3 and 4.

Figure 3:
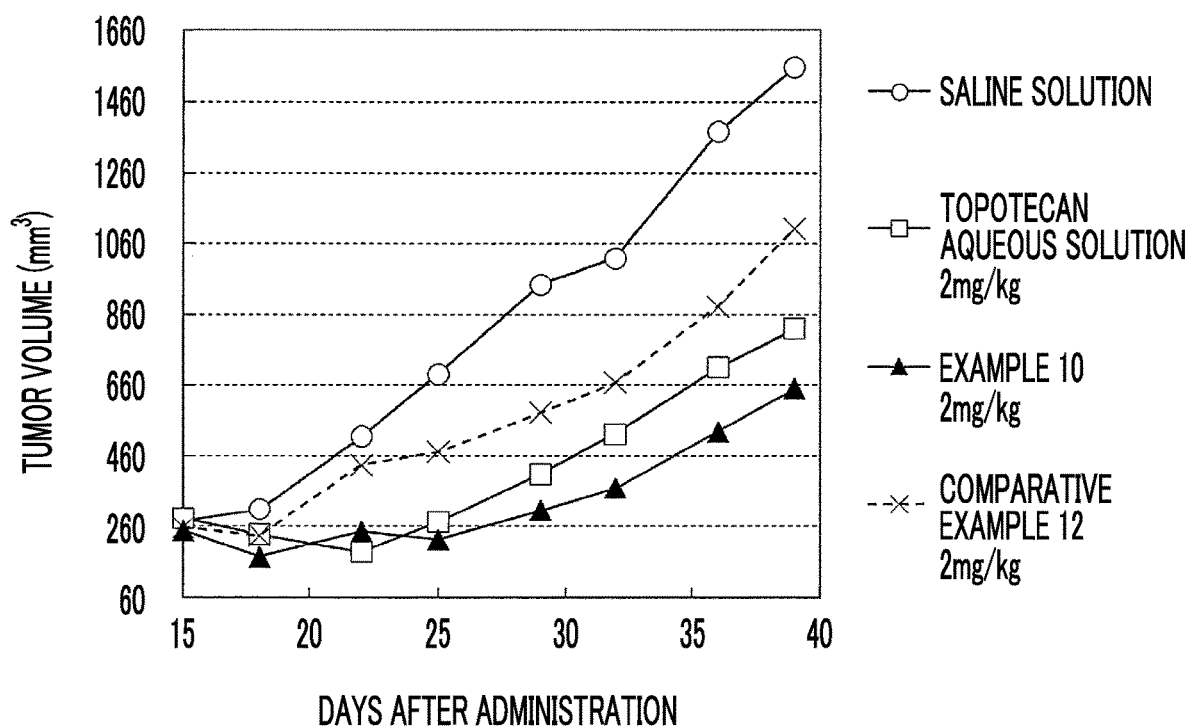
FIG. 3 shows the measurement results of tumor volume in a drug efficacy test using an A549 subcutaneous transplantation mouse model.
Figure 4:
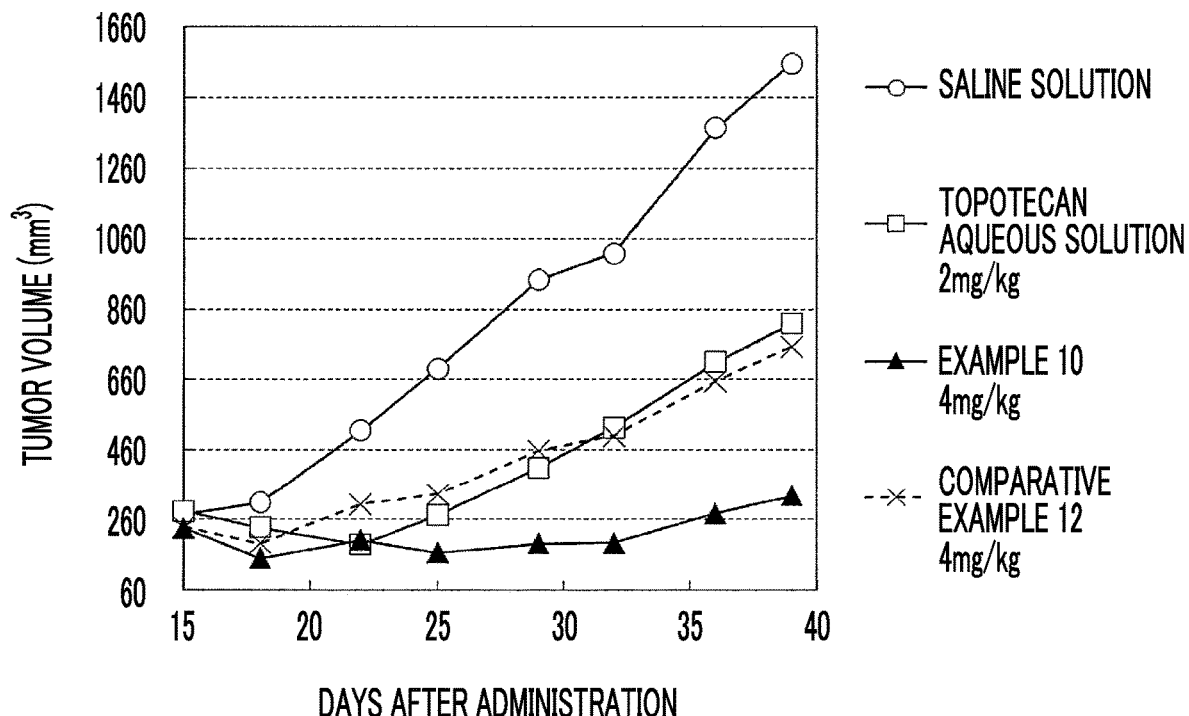
FIG. 4 shows the measurement results of tumor volume in a drug efficacy test using an A549 subcutaneous transplantation mouse model.

From the results of FIGS. 3 and 4, it was demonstrated that the topotecan-containing liposome prepared in Example 10 exhibits higher drug efficacy as compared with the topotecan solution prepared in Comparative Example 12, and the effect is dose-dependent.

Examples 11 to 16 and Comparative Examples 13 to 16

Topotecan-containing liposomes were prepared in the same manner as in Example 1, except that, for Examples 11 to 16, the amounts of DHSM, DSPE-PEG, and cholesterol were changed so that the addition amount of cholesterol and the addition amount of chicken egg-derived DHSM in adjusting of the oil phase become the ratios described in Table 3. For example, for Example 11, topotecan-containing liposomes were produced in the same manner as in Example 1, except that the addition amount of cholesterol and the addition amount of chicken egg-derived DHSM in adjusting of the oil phase were changed to 3.6 g of cholesterol and 12.9 g of chicken egg-derived DHSM.

For Comparative Examples 13 to 16, the amounts of SM, DSPE-PEG, and cholesterol were changed to the ratios described in Table 3.

Figure 5:
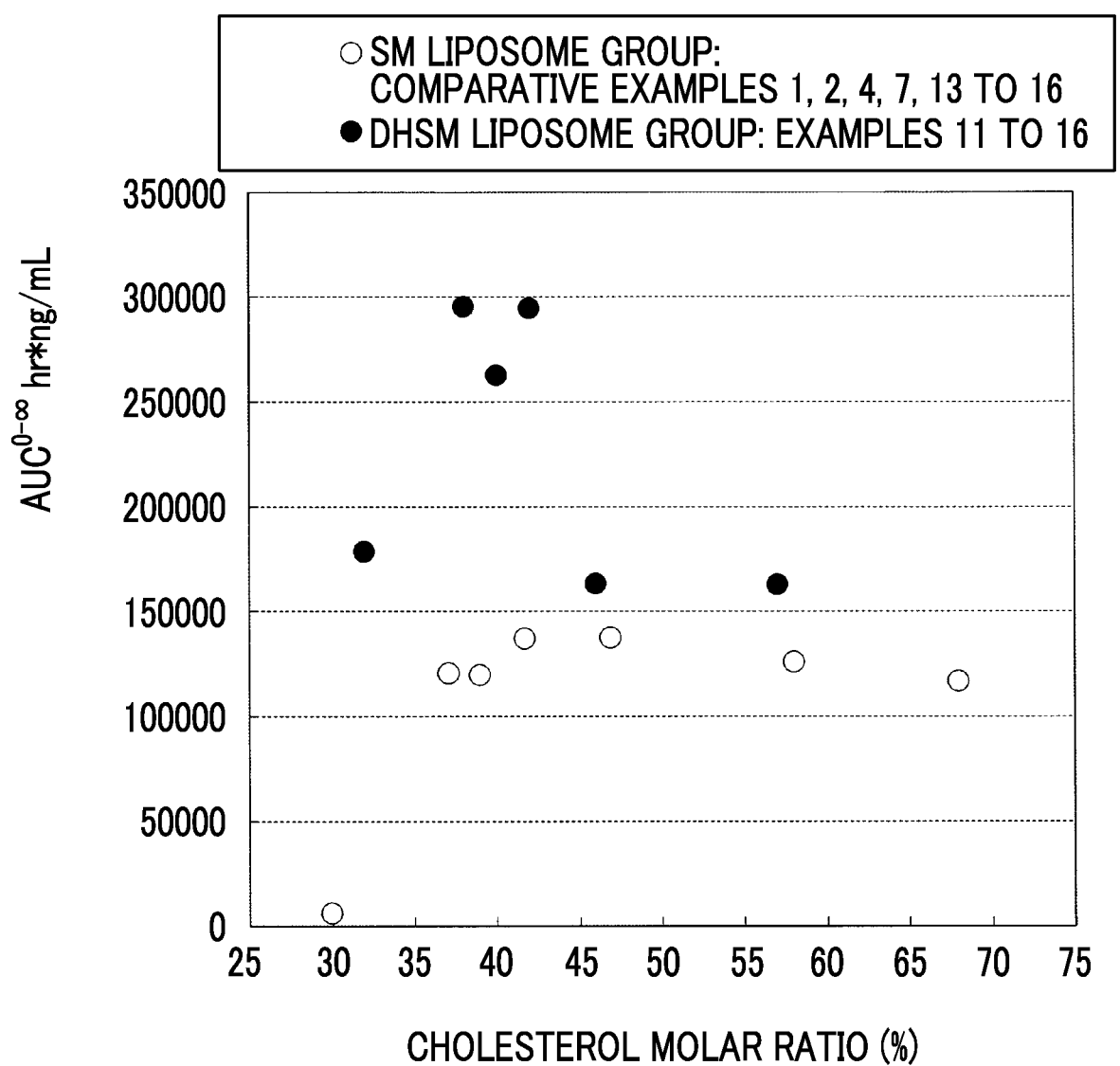
FIG. 5 shows the value of AUC for each amount of cholesterol.

Similarly, the results of measuring the particle size, concentration of topotecan in the entire water phase, concentration of sulfate ions in the inner water phase, and AUC are shown in Table 3. In addition, the value of AUC for each amount of cholesterol is shown in FIG. 5.

In the liposomes of Table 3, the percentage of the drug contained in the inner water phase of the liposome to the drug in the entire liposome composition was at least 98%, except for Comparative Example 13 in which the percentage of the drug contained in the inner water phase of the liposome to the drug in the entire liposome composition was 68%.

In the liposomes of Table 3, the percentage of sulfate ions contained in the inner water phase of the liposome to the sulfate ions in the entire liposome composition was at least 90% except for Comparative Example 13 in which the percentage of sulfate ions contained in the inner water phase of the liposome to sulfate ions in the entire liposome composition was 71%.

TABLE 3

| | Average particle size | Concentration of topotecan in entire water phase | $SO_4^{2-}$ in inner water phase/ topotecan in entire water phase | Molar ratio of components of liposome membrane | | | | Dose | AUC | Percentage of topotecan in inner water phase | Percentage of $SO_4^{2-}$ in inner water phase |
|---|---|---|---|---|---|---|---|---|---|---|---|
| | | | | PEG | Chol | DHSM | SM | | | | |
| | nm | ppm | mol/mol | | | | | mg/kg | hr * ng/mL | % | % |
| Example 11 | 97 | 2516 | 0.76 | 5.0 | 32.0 | 63.0 | 0 | 1 | 194404 | 99 | 93 |
| Example 12 | 111 | 2167 | 1.05 | 5.2 | 37.6 | 57.1 | 0 | 1 | 295476 | 99 | 98 |
| Example 13 | n.d. | 2533 | 0.78 | 5.0 | 40.0 | 55.0 | 0 | 1 | 262734 | 99 | 100 |
| Example 14 | 118 | 2240 | 0.89 | 5.1 | 42.4 | 52.5 | 0 | 1 | 294694 | 100 | 100 |
| Example 15 | 96 | 2163 | 0.38 | 5.0 | 48.0 | 47.0 | 0 | 1 | 163010 | 100 | 100 |
| Example 16 | 102 | 2559 | 0.50 | 4.0 | 57.0 | 39.0 | 0 | 1 | 162607 | 100 | 100 |
| Comparative Example 13 | 119.5 | 720 | 0.81 | 4.7 | 27.0 | 0 | 68.3 | 1 | 5940 | 68 | 71 |
| Comparative Example 14 | 112 | 2311 | 0.80 | 4.7 | 37.1 | 0 | 58.2 | 1 | 120189 | 100 | 100 |
| Comparative Example 15 | 105 | 2746 | 1.28 | 4.6 | 58.5 | 0 | 36.9 | 1 | 125814 | 99 | 97 |
| Comparative Example 16 | 106 | 2529 | 1.28 | 4.8 | 68.3 | 0 | 26.9 | 1 | 116623 | 99 | 97 |

Example 16

From the results of Examples 11 to 16 and Comparative Examples 1, 2, 4, 7, and 13 to 16, it can be seen that the present invention achieves a satisfactory AUC for liposomes with chicken egg-derived DHSM at a wider loading percentage of cholesterol than SM liposomes. In addition, in the chicken egg-derived DHSM liposome of the present invention, it can be seen that the AUC is more satisfactory, in particular, in a case where the percentage of cholesterol is in the range of 35 to 43 mol %.

Examples 17 to 24 and Comparative Examples 17 to 24

<Preparation of Liposome Dispersion Liquid>

Topotecan-containing liposomes were prepared in the same manner as in Example 1, except that, for Examples 17 to 24 and Comparative Examples 17 to 24, the addition amount of each lipid in adjusting of the oil phase was set as shown in Table 4, the drug to be encapsulated in the liposome particles by remote loading was set as shown in Table 4, and the drugs other than topotecan were encapsulated by the method described in the section <Encapsulation of each anticancer drug in liposome particles by remote loading> described below. In addition, the lipid composition ratio in each of Examples 17 to 24 and Comparative Examples 17 to 24 is shown in Table 5.

TABLE 4

| | Totally synthetic DHSM/g | Chicken egg DHSM/g | Chol/ g | PEG/ g | Drug type |
|---|---|---|---|---|---|
| Example 17 | 11.52 | — | 4.32 | 4.32 | Topotecan |
| Example 18 | — | 11.52 | 4.32 | 4.32 | Topotecan |
| Example 19 | 11.52 | — | 4.32 | 4.32 | Doxorubicin |
| Example 20 | — | 11.52 | 4.32 | 4.32 | Doxorubicin |
| Example 21 | 11.52 | — | 4.32 | 4.32 | Sunitinib |
| Example 22 | — | 11.52 | 4.32 | 4.32 | Sunitinib |
| Example 23 | 11.52 | — | 4.32 | 4.32 | Irinotecan |
| Example 24 | — | 11.52 | 4.32 | 4.32 | Irinotecan |
| Comparative Example 17 | 11.52 | — | 4.32 | 4.32 | Topotecan |

TABLE 4-continued

| | Totally synthetic DHSM/g | Chicken egg DHSM/g | Chol/ g | PEG/ g | Drug type |
|---|---|---|---|---|---|
| Comparative Example 18 | — | 12.98 | 4.26 | 4.20 | Topotecan |
| Comparative Example 19 | 11.52 | — | 4.32 | 4.32 | Doxorubicin |
| Comparative Example 20 | — | 12.98 | 4.26 | 4.20 | Doxorubicin |
| Comparative Example 21 | 11.52 | — | 4.32 | 4.32 | Sunitinib |
| Comparative Example 22 | — | 12.98 | 4.26 | 4.20 | Sunitinib |
| Comparative Example 23 | 11.52 | — | 4.32 | 4.32 | Irinotecan |
| Comparative Example 24 | — | 12.98 | 4.26 | 4.20 | Irinotecan |

TABLE 5

| | Molar ratio | | | | | |
|---|---|---|---|---|---|---|
| | PEG | Chol | DHSM | SM | Totally synthetic DHSM | HSPC |
| Example 17 | 5% | 39% | 0% | 0% | 56% | 0% |
| Example 18 | 5% | 39% | 56% | 0% | 0% | 0% |
| Example 19 | 5% | 39% | 0% | 0% | 56% | 0% |
| Example 20 | 5% | 39% | 56% | 0% | 0% | 0% |
| Example 21 | 5% | 39% | 0% | 0% | 56% | 0% |
| Example 22 | 5% | 39% | 56% | 0% | 0% | 0% |
| Example 23 | 5% | 38% | 0% | 0% | 56% | 0% |
| Example 24 | 5% | 38% | 57% | 0% | 0% | 0% |
| Comparative Example 17 | 5% | 37% | 0% | 58% | 0% | 0% |
| Comparative Example 18 | 5% | 41% | 0% | 0% | 0% | 54% |
| Comparative Example 19 | 5% | 36% | 0% | 59% | 0% | 0% |
| Comparative Example 20 | 5% | 41% | 0% | 0% | 0% | 54% |
| Comparative Example 21 | 5% | 37% | 0% | 59% | 0% | 0% |
| Comparative Example 22 | 5% | 41% | 0% | 0% | 0% | 53% |
| Comparative Example 23 | 4% | 37% | 0% | 59% | 0% | 0% |

TABLE 5-continued

| | Molar ratio | | | | | |
|---|---|---|---|---|---|---|
| | PEG | Chol | DHSM | SM | Totally synthetic DHSM | HSPC |
| Comparative Example 24 | 5% | 41% | 0% | 0% | 0% | 54% |

<Encapsulation of Each Anticancer Agent in Liposome Particles by Remote Loading>

Encapsulation of doxorubicin (Examples 19 and 20, and Comparative Examples 19 and 20): Water for injection was added to doxorubicin hydrochloride (manufactured by Tokyo Chemical Industry Co., Ltd.) to 4 mg/mL. Further, while stirring the liquid well, an 8 mol/L HCl solution was added to adjust the pH to about 3 to dissolve doxorubicin hydrochloride. Liposomes were added to the resulting doxorubicin solution at a volume ratio of 1/1, and then the dispersion liquid adjusted to pH 7.0 was heated at 62° C. for 60 minutes.

Encapsulation of sunitinib (Examples 21 and 22, and Comparative Examples 21 and 22): Water for injection was added to sunitinib malate (manufactured by Toronto Research Chemicals Inc.) to 5 mg/mL. Further, while stirring the liquid well, an 8 mol/L HCl solution was added to adjust the pH to about 3 to dissolve sunitinib malate. Liposomes were added to the resulting sunitinib solution at a volume ratio of 1/1, followed by heating at 62° C. for 60 minutes.

Encapsulation of irinotecan (Examples 23 and 24, and Comparative Examples 23 and 24): Water for injection was added to irinotecan hydrochloride (manufactured by Tokyo Chemical Industry Co., Ltd.) to 4 mg/mL. Further, while stirring the liquid well, an 8 mol/L HCl solution was added to adjust the pH to about 3 to dissolve irinotecan hydrochloride. Liposomes were added to the resulting irinotecan solution at a volume ratio of 1/1, followed by heating at 62° C. for 60 minutes.

The AUC in Examples 17 to 22 and Comparative Examples 17 to 22 was measured in the same manner as described above in the present Examples. The results are shown in Table 6.

TABLE 6

| | Drug | Lipid | AUC hr * ng/mL |
|---|---|---|---|
| Example 17 | Topotecan | Totally synthetic DHSM | 227177 |
| Example 18 | Topotecan | Chicken egg-derived DHSM | 201266 |
| Comparative Example 17 | Topotecan | SM | 164034 |
| Comparative Example 18 | Topotecan | HSPC | 86692 |
| Example 19 | Doxorubicin | Totally synthetic DHSM | 506246 |
| Example 20 | Doxorubicin | Chicken egg-derived DHSM | 539688 |
| Comparative Example 19 | Doxorubicin | SM | 481802 |
| Comparative Example 20 | Doxorubicin | HSPC | 433691 |
| Example 21 | Sunitinib | Totally synthetic DHSM | 37661 |
| Example 22 | Sunitinib | Chicken egg-derived DHSM | 26421 |
| Comparative Example 21 | Sunitinib | SM | 19904 |
| Comparative Example 22 | Sunitinib | HSPC | 6453 |

From the results of Examples 17 to 22 and Comparative Examples 17 to 22, even in a case where either drug of topotecan or sunitinib was used, liposomes using DHSM exhibited improved retention in blood as compared to SM liposomes and HSPC liposomes. In addition, it was found that liposomes using totally synthetic DHSM having a purity of 98% or more of DHSM having an alkyl chain having 16 carbon atoms and an alkyl chain having 18 carbon atoms as DHSM are capable of improving retention in blood as compared to liposomes using chicken egg-derived DHSM.

The particle size, topotecan concentration, sulfate ion concentration, and release rate in Examples 17 to 24 and Comparative Examples 17 to 18 and 21 to 24 were measured. The results are shown in Table 7. The particle size, topotecan concentration, and sulfate ion concentration were measured in the same manner as described above in the present Examples.

In the liposomes of Table 7, the percentage of the drug contained in the inner water phase of the liposomes to the drug of the entire liposome composition was at least 95%.

In the liposomes of Table 7, the percentage of sulfate ions contained in the inner water phase of the liposome to sulfate ions in the entire liposome composition was at least 95%.

The liposome formulation was diluted 20-fold in each concentration of ammonium chloride-containing PBS buffer, and the release rate thereof after incubation for 4 hours was measured. The release rate is defined as the percentage of the API concentration leaked to the outer water phase divided by the initial API concentration in the entire water phase.

For each concentration of ammonium chloride-containing PBS buffer, in Examples 17 and 18 and Comparative Examples 17 and 18 (evaluation of topotecan-encapsulated liposomes), a PBS buffer in which 4.8 mmol/L of ammonium chloride was dissolved was used, in Examples 19 and 20 and Comparative Examples 19 and 20 (evaluation of doxorubicin-encapsulated liposomes), a PBS buffer in which 200 mmol/L of ammonium chloride was dissolved was used, in Examples 21 and 22 and Comparative Examples 21 and 22 (evaluation of sunitinib-encapsulated liposomes), a PBS buffer in which 100 mmol/L of ammonium chloride was dissolved was used, and in Examples 23 and 24 and Comparative Examples 23 and 24 (evaluation of irinotecan-encapsulated liposomes), a PBS buffer in which 4.8 mmol/L of ammonium chloride was dissolved was used.

TABLE 7

| | Drug | Lipid | Concentration of drug in entire water phase ppm | $SO_4^{2-}$ in inner water phase/drug in entire water phase mol/mol | Release rate % | Percentage of drug in inner water phase % | Percentage of $SO_4^{2-}$ in inner water phase % |
|---|---|---|---|---|---|---|---|
| Example 17 | Topotecan | Totally synthetic DHSM | 2160 | 1.25 | 18 | 99 | 99 |
| Example 18 | Topotecan | Chicken egg DHSM | 2813 | 1.53 | 33 | 100 | 99 |
| Comparative Example 17 | Topotecan | SM | 2341 | 1.55 | 59 | 99 | 99 |
| Comparative Example 18 | Topotecan | HSPC | 2308 | 0.98 | 62 | 99 | 97 |
| Example 19 | Doxorubicin | Totally synthetic DHSM | 1924 | 1.90 | 1 | 100 | 98 |
| Example 20 | Doxorubicin | Chicken egg DHSM | 2138 | 2.39 | 2 | 100 | 98 |
| Example 23 | Irinotecan | Totally synthetic DHSM | 2373 | 1.72 | 5 | 100 | 99 |
| Example 24 | Irinotecan | Chicken egg DHSM | 2827 | 2.19 | 13 | 100 | 99 |
| Comparative Example 23 | Irinotecan | SM | 2512 | 2.13 | 27 | 99 | 99 |
| Comparative Example 24 | Irinotecan | HSPC | 2486 | 1.31 | 36 | 99 | 97 |
| Example 21 | Sunitinib | Totally synthetic DHSM | 2022 | 1.39 | 7 | 100 | 99 |
| Example 22 | Sunitinib | Chicken egg DHSM | 2263 | 1.92 | 5 | 100 | 98 |
| Comparative Example 21 | Sunitinib | SM | 2206 | 1.67 | 8 | 100 | 100 |
| Comparative Example 22 | Sunitinib | HSPC | 2203 | 0.96 | 8 | 100 | 98 |

According to the results of Examples 17 to 24 and Comparative Examples 17, 18 and 21 to 24, the release rate of the liposomes using DHSM is lower than that of the SM liposomes and the HSPC liposomes, regardless of which agent is used, from which an improvement of retention in blood can be expected. In addition, in a case where DHSM is a totally synthetic DHSM having a purity of 98% or more with an alkyl chain having 16 carbon atoms and an alkyl chain having 18 carbon atoms, the release rate is greatly reduced in the topotecan-encapsulated liposome, doxorubicin-encapsulated liposome, and irinotecan-encapsulated liposome, and therefore use of such totally synthetic DHSM has been found to be more preferable in suppressing leakage of the drug in blood.

<Measurement of Insoluble Particulates>

For each of Examples 2, 3, and 4, the samples one month after storage at 5° C. were measured in a submerged particle counter (HACH ULTRA), and the number of particles of more than 10 μm and the number of particles of more than 25 μm contained per vial formulation (2 mL) were measured (hereinafter, unless otherwise specified, particles of more than 10 μm refer to particles of more than 10 μm in particle size, and particles of more than 25 μm refer to particles of more than 25 μm in particle size). The lipid concentration in Examples 2, 3, and 4 was 23 mmol/L, and the number of particles per 1 μmol of lipid for particles of more than 10 μm was 0.7 for Example 2, 1.1 for Example 3, and 0.3 for Example 4. In addition, the number of particles per 1 μmol of lipid for particles of more than 25 μm was 0.09 for Example 2, 0.5 for Example 3, and 0 for Example 4. Topotecan-encapsulated liposomes are known to break into poorly soluble dimers in a case of being leaked and exposed to a neutral environment, thus becoming insoluble particulates. This is a surprising result that the generation of insoluble particulates has also been reduced because the leakage is extremely well suppressed by the present invention.

For Comparative Example 8, the insoluble particulates in 1 vial formulation (2 mL) were measured also in the sample one month after 5° C. In terms of the number of particles per 1 μmol of lipid, the number of particles of more than 10 μm was 251, thus greatly exceeding 150, and the number of particles of more than 25 μm was 17, thus greatly exceeding 15.

<Dependence of Ammonium Ion on Release Rate>

Figure 6:
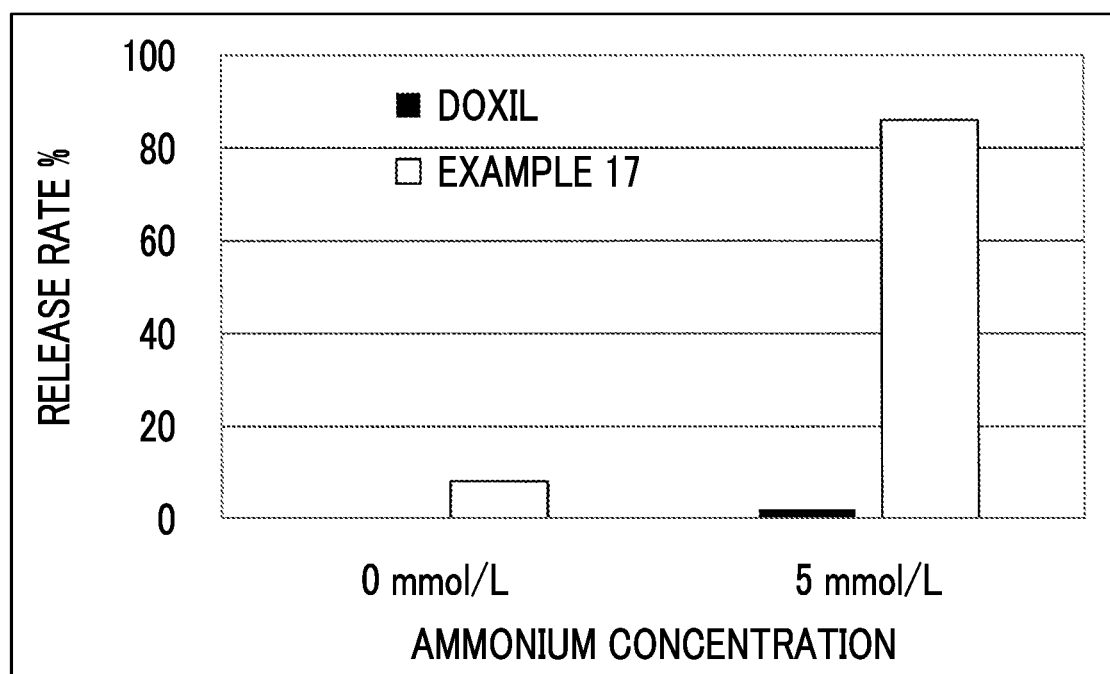
FIG. 6 shows the measurement results of ammonium ion dependence on release rate.

The release rate was calculated as the percentage of the concentration of leaked drug (concentration of drug in outer water phase) to the concentration of drug in the entire water phase. For topotecan-encapsulated DHSM liposomes prepared in Example 17, and doxorubicin-encapsulated HSPC liposomes (Doxil (registered trademark) 20MG, available from Janssen Pharma, Inc.), the release rate of the liposomes was measured in plasma without addition of ammonium chloride (manufactured by LAMPIRE Biological Laboratories, Inc., mouse plasma, product name: Control and Donor Mouse Plasma in Na Hep, Catalog No. 7315511) and plasma in which 5 mmol/L of ammonium chloride was dissolved. The results are shown in FIG. 6. In the tumor environment, glutamine degradation is enhanced, and as a result, a large amount of ammonium is generated, for which the occurrence of approximately 5 mmol/L of ammonium has been reported (cited article: Nanomedicine: Nanotechnology, Biology, and Medicine, 11 (2015) 1841-1850).

Doxil (registered trademark) 20MG is a doxorubicin-encapsulated liposome composed of HSPC. Doxil (registered trademark) exhibits very little leakage in an environment that mimics blood, but has been found to be virtually non-releasing even in a high ammonium environment that mimics the tumor environment.

On the other hand, the liposome containing topotecan, which is described in Example 17 of the present invention, exhibits very low leakage in an environment that mimics blood, thus resulting in high retention in blood, whereas it exhibits very high release of 86% in a high ammonium environment that mimics the tumor environment and does not leak in blood, thus leading to the result of an expectation that a high amount of the drug is delivered to the tumor by the liposome and the drug carried by the liposome is released in large amounts in the tumor. The results are shown in FIG. 6.

In addition, a tumor obtained by actually transplanting a human ovarian cancer cell line ES-2 subcutaneously into a BALB/c nude mouse was collected and placed on a 5 μm pore size centrifugal filter, followed by centrifugation at 400 g for 10 minutes to obtain a tumor interstitial fluid. The topotecan liposomes (30 ng in terms of the amount of drug) of the present invention prepared in Example 17 and doxorubicin-encapsulated HSPC liposomes (Doxil (registered trademark) 20MG, available from Janssen Pharma, Inc.) (30 ng in terms of the amount of drug) were respectively added to 30 μL of the tumor interstitial fluid, followed by incubation. The release rate in a case of incubation at 37° C. for 24 hours was 85% in Example 17 and 6% in doxorubicin-encapsulated HSPC liposomes, thus showing that a difference in release was observed as expected in the tumor interstitial fluid collected from the actual tumor environment.

What is claimed is:

1. A liposome composition comprising: liposomes each of which has an inner water phase and an aqueous solution which constitutes an outer water phase and in which the liposomes are dispersed,
    wherein the liposomes comprise
    a hydrophilic polymer-modified diacylphosphatidylethanolamine,
    a dihydrosphingomyelin, and cholesterols
    wherein each of the liposomes encapsulates a drug,
    the inner water phase contains ammonium sulfate,
    and the molar ratio of sulfate ions in the inner water phase to the sum of the drug contained in the inner water phase and the outer water phase is 0.6 or more and 1.8 or less.

2. The liposome composition according to claim 1, wherein the drug is an anticancer drug.

3. The liposome composition according to claim 1, wherein the drug is an anthracycline-based anticancer agent, a cisplatin-based anticancer agent, a taxane-based anticancer agent, a vinca alkaloid-based anticancer agent, a bleomycin-based anticancer agent, a sirolimus-based anticancer agent, a camptothecin-based anticancer agent, a metabolic antagonists, or a molecularly targeted drug.

4. The liposome composition according to claim 1, wherein the drug is topotecan or a salt thereof, doxorubicin or a salt thereof, irinotecan or a salt thereof, or sunitinib or a salt thereof.

5. The liposome composition according to claim 1, wherein the hydrophilic polymer-modified diacylphosphatidylethanolamine is a polyethylene glycol- or methoxy polyethylene glycol-modified diacylphosphatidylethanolamine.

6. The liposome composition according to claim 1, wherein the percentage of the hydrophilic polymer-modified diacylphosphatidylethanolamine in the liposome is 2 to 10 mol %.

7. The liposome composition according to claim 1, wherein the percentage of cholesterols in the liposome is 35 to 43 mol %.

8. The liposome composition according to claim 1, wherein the liposomes have a particle size of 30 nm to 150 nm.

9. The liposome composition according to claim 1, wherein the outer water phase has a pH of 5.5 to 8.5.

10. The liposome composition according to claim 1, wherein the dihydrosphingomyelin is a dihydrosphingomyelin containing a long-chain alkyl group having 16 carbon atoms and a long-chain alkyl group having 18 carbon atoms, and the drug is topotecan or a salt thereof.

11. The liposome composition according to claim 1, wherein the percentage of the sulfate ions contained in the inner water phase of the liposome to the sulfate ions in the entire liposome composition is at least 80%, and the percentage of the drug contained in the inner water phase of the liposome to the drug in the entire liposome composition is at least 80%.

12. The liposome composition according to claim 10, wherein the drug release rate from the liposome in plasma having an ammonium concentration of 1 mmol/L or less is 20%/24 hours or less at 37° C., and the drug release rate from the liposome in plasma having an ammonium concentration of 4 to 6 mmol/L is 60%/24 hours or more at 37° C.

13. The liposome composition according to claim 1, wherein the number of insoluble particles of more than 10 μm contained in 1 μmol of lipid of the liposome composition after storage for 1 month at 5° C. is 150 or less, and the number of insoluble particles of more than 25 μm contained in 1 μmol of lipid of the liposome composition is 15 or less.

14. A pharmaceutical composition comprising:
    the liposome composition according to claim 1.

15. A method for treating an anticancer disease, comprising administering the pharmaceutical composition according to claim 14.

* * * * *